(12) United States Patent
Stevenazzi et al.

(10) Patent No.: US 10,590,101 B2
(45) Date of Patent: Mar. 17, 2020

(54) BENZO-N-HYDROXY AMIDE COMPOUNDS HAVING ANTITUMOR ACTIVITY

(71) Applicant: ITALFARMACO SPA, Milan (IT)

(72) Inventors: Andrea Stevenazzi, Milan (IT); Giovanni Sandrone, Novara (IT); Daniela Modena, Monza (IT); Samuele Pietro Pozzi, Legnano (IT); Barbara Vergani, Macherio (IT); Maria Lattanzio, Milan (IT); Paolo Mascagni, Alicante (ES); Christian Steinkühler, Rome (IT); Gianluca Fossati, Milan (IT)

(73) Assignee: ITALFARMACO SPA, Milan (IT)

( * ) Notice: Subject to any disclaimer, the term of this patent is extended or adjusted under 35 U.S.C. 154(b) by 0 days.

(21) Appl. No.: 16/315,576

(22) PCT Filed: Jul. 14, 2017

(86) PCT No.: PCT/EP2017/067850
§ 371 (c)(1),
(2) Date: Jan. 4, 2019

(87) PCT Pub. No.: WO2018/015292
PCT Pub. Date: Jan. 25, 2018

(65) Prior Publication Data
US 2019/0300496 A1  Oct. 3, 2019

(30) Foreign Application Priority Data

Jul. 18, 2016  (IT) .............................. 1020160074606

(51) Int. Cl.
C07D 317/60 (2006.01)
C07D 215/14 (2006.01)
C07D 407/12 (2006.01)
C07D 213/643 (2006.01)
C07D 209/18 (2006.01)
A61P 35/00 (2006.01)
C07C 259/10 (2006.01)
C07D 213/56 (2006.01)
C07D 221/04 (2006.01)
C07D 233/64 (2006.01)
C07D 405/12 (2006.01)
C07D 409/12 (2006.01)
C07D 417/12 (2006.01)
A61K 31/165 (2006.01)
A61K 31/357 (2006.01)
A61K 31/4035 (2006.01)
A61K 31/443 (2006.01)
A61K 31/47 (2006.01)
C07D 317/06 (2006.01)

(52) U.S. Cl.
CPC ............ C07D 317/60 (2013.01); A61P 35/00 (2018.01); C07C 259/10 (2013.01); C07D 209/18 (2013.01); C07D 213/56 (2013.01);
C07D 213/643 (2013.01); C07D 215/14 (2013.01); C07D 221/04 (2013.01); C07D 233/64 (2013.01); C07D 405/12 (2013.01); C07D 407/12 (2013.01); C07D 409/12 (2013.01); C07D 417/12 (2013.01)

(58) Field of Classification Search
CPC .. C07D 317/60; C07D 221/04; C07D 213/56; C07D 417/12; C07D 409/12; C07D 405/12; C07D 233/64; C07D 215/14; C07D 407/12; C07D 213/643; C07D 209/18; C07D 317/06; A61P 35/00; C07C 259/10; A61K 31/165; A61K 31/357; A61K 31/4035; A61K 31/443; A61K 31/47
See application file for complete search history.

(56) References Cited

U.S. PATENT DOCUMENTS 7,635,788 B2   12/2009  Pinori et al.

FOREIGN PATENT DOCUMENTS

WO   2006/003068 A2   1/2006

OTHER PUBLICATIONS

Neidle, Stephen, ed. Cancer drug design and discovery. Academic Press, 2008, p. 427-431.*
Luo, J., "Principles of cancer therapy: oncogene and non-oncogene addiction." Cell 136.5 (2009): 823-837.*
(Continued)

Primary Examiner — John M Mauro
(74) Attorney, Agent, or Firm — Perkins Coie LLP; Viola T. Kung

(57) ABSTRACT

The present invention relates to new benzo-N-hydroxy amide compounds of formula (I) and pharmaceutically acceptable salts, isomers and prodrugs thereof, which show a significant inhibitory activity on the proliferation of tumor cells and specifically of cancer stem cells.

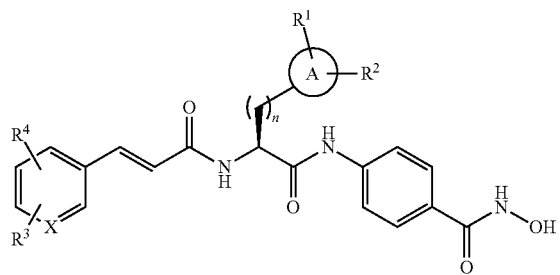

10 Claims, No Drawings

(56) References Cited

OTHER PUBLICATIONS

Leaf, C., "Why we're losing the war on cancer (and how to win it)." (2005) Health Administrator vol. XVJJ, No. 1: 172-183.*
Kamb, A., "What's wrong with our cancer models?." Nature reviews Drug discovery 4.2 (2005): 161-165.*
Gura, T., "Systems for identifying new drugs are often faulty." Science (1997) 278 (5340): 1041-1042.*
Burtles, S., Expert Scientific Group on Phase One Clinical Trials (Great Britain). Expert Scientific Group on Phase One Clinical Trials: Final Report: Nov. 30, 2006. TSO, 2006.*
Skin Cancer Foundation (Melanoma Prevention Guidelines 2015, obtained from https://www.skincancer.org/skin-cancer-prevention.*
Hrabeta, J., "Histone deacetylase inhibitors in cancer therapy. A review." Biomedical Papers 158.2 (2014): 161-169).*
Li, X., et al., "Development of N-hydroxybenzamide derivatives with indole-containing cap group as histone deacetylases inhibitors," Bioorganic & Medicinal Chemistry, vol. 23, Issue 19, Oct. 1, 2015, pp. 6258-6270.
Berge, S.M., "Pharmaceutical Salts," Journal of Pharmaceutical Sciences, vol. 66, No. 1, Jan. 1977, pp. 1-19.
Botchkina, I.L., et al., "Phenotypic Subpopulations of Metastatic Colon Cancer Stem Cells: Genomic Analysis," Cancer Genomics & Proteomics 6:19-30 (2009).
Schlimme, S., et al., "Carbamate Prodrug Concept for Hydroxamate HDAC Inhibitors," ChemMedChem (2011), 6, 1193-1198.
Pfannkuch, F., et al., "Biological Effects of the Drug Salt Form," Handbook of Pharmaceutical Salts, International Union of Pure and Applied Chemistry (IUPAC) (2008) pp. 127-133.
Shirote, P.J., et al., "Prodrug Approach: An Effective Solution to Overcome Side-Effects," International Journal of Medical and Pharmaceutical Sciences, vol. 1(7), (2011), pp. 1-13.
Yeung, T.M., "Cancer stem cells from colorectal cancer-derived cell lines," PNAS, vol. 107(8), Feb. 23, 2010, 3722-3727.
International Search Report PCT/EP2017/067850 dated Jun. 9, 2017, 4 pages.

* cited by examiner

BENZO-N-HYDROXY AMIDE COMPOUNDS HAVING ANTITUMOR ACTIVITY

This application is a National Stage of International Application PCT/EP2017/067850, filed Jul. 14, 2017, published Jan. 25, 2018 under PCT Article 21(2) in English; which claims the priority of Italian Application No. 102016000074606, filed Jul. 18, 2016. The contents of the above-identified applications are incorporated herein by reference in their entireties.

FIELD OF THE INVENTION

The present invention relates to new benzo-N-hydroxy amide compounds having an alpha-amino acidic scaffold carrying an alpha-beta unsaturated carbonyl moiety on the amino-group and to the pharmaceutical compositions thereof.

The molecules have antitumor activity and are particularly active on cancer stem cells.

BACKGROUND OF THE INVENTION

Partial or even complete cancer regression can be achieved in some patients with current cancer treatments. However, such initial responses are almost always followed by relapse, with the recurrent cancer being resistant to further treatments. The discovery of therapeutic approaches that counteract relapse is, therefore, essential for advancing cancer medicine. Cancer cells are extremely heterogeneous, even in each individual patient, in terms of their malignant potential, drug sensitivity, and their potential to metastasize and cause relapse. Indeed, hypermalignant cancer cells, termed cancer stem cells or tumor-initiating cells, that are highly tumorigenic and metastatic have been isolated from cancer patients with a variety of tumor types. Moreover, such stemness-high cancer cells are resistant to conventional chemotherapy and radiation.

Therefore, development of specific therapies targeted at cancer stem cells holds hope for improvement of survival and quality of life of cancer patients, especially for patients with metastatic disease.

U.S. Pat. No. 7,635,788 discloses hydroxamic acid derivatives containing an alpha-aminoacyl moiety and having inhibitory activity on the proinflammatory cytokines production, in particular TNFα. Such compounds are useful in the treatment of inflammatory diseases and other disorders characterised by overproduction of TNFα or other proinflammatory cytokines. Said compounds furthermore exhibit a cytotoxicity activity in in vitro testing on human hepatoma cell line Hep-G2.

Definitions

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The term "halogen" herein refers to fluorine (F), chlorine (Cl), bromine (Br), or iodine (I).

The term "$C_1$-$C_4$ alkyl" herein refers to a branched or linear hydrocarbon containing from 1 to 4 carbon atoms. Examples of $C_1$-$C_4$ alkyl groups include but are not limited to methyl, ethyl, n-propyl, isopropyl, n-butyl, sec-butyl, isobutyl, tert-butyl.

The term "aryl" herein refers to aromatic mono- and poly-carbocyclic ring systems, wherein the individual carbocyclic rings in the poly-carbocyclic ring systems may be fused or attached to each other via a single bond. Suitable aryl groups include, but are not limited to, phenyl, naphthyl and biphenyl.

The term "aryloxy" herein refers to O-aryl group, wherein "aryl" is defined above.

The term "alkoxy" herein refers to O-alkyl group, wherein "alkyl" is defined above.

The term "arylalkyl" herein refers to an aryl radical, as defined herein, attached to an alkyl radical, as defined herein.

The term "arylcarbonyl" herein refers to —C(O)-aryl, wherein "aryl" is defined above.

The term "heterocycle" herein refers to a 4-, 5-, 6-, 7- or 8-membered monocyclic ring which is saturated or unsaturated, and which consists of carbon atoms and one or more heteroatoms selected from N, O and S, and wherein the nitrogen and sulphur heteroatoms may optionally be oxidized, and the nitrogen heteroatom may optionally be quaternized. The heterocycle ring may be attached to any heteroatom or carbon atom, provided that attachment results in the creation of a stable structure. The term also includes any bicyclic system in which any of the above heterocyclic rings is fused to an aryl or another heterocycle. When the heterocycle ring is an aromatic heterocycle ring it can be defined "heteroaromatic ring".

The terms "comprising", "having", "including" and "containing" are to be construed as open-ended terms (i.e. meaning "including, but not limited to") and are to be considered as providing support also for terms as "consist essentially of", "consisting essentially of", "consist of" or "consisting of".

The terms "consist essentially of", "consisting essentially of" are to be construed as a semi-closed terms, meaning that no other ingredients and/or steps which materially affects the basic and novel characteristics of the invention are included (optional excipients may be thus included).

The terms "consists of", "consisting of" are to be construed as a closed term.

The term "pharmaceutically acceptable salts" herein refers to those salts which possess the biological effectiveness and properties of the salified compound and which do not produce adverse reactions when administered to a mammal, preferably a human. The pharmaceutically acceptable salts may be inorganic or organic salts; examples of pharmaceutically acceptable salts include but are not limited to: carbonate, hydrochloride, hydrobromide, sulphate, hydrogen sulphate, citrate, maleate, fumarate, acetate, trifluoroacetate, pamoate, 2-naphthalenesulphonate, and para-toluenesulphonate. Further information on pharmaceutically acceptable salts can be found in Handbook of pharmaceutical salts, P. Stahl, C. Wermuth, WILEY-VCH, 127-133, 2008, herein incorporated by reference.

The term "physiologically acceptable excipient" herein refers to a substance devoid of any pharmacological effect of its own and which does not produce adverse reactions when administered to a mammal, preferably a human. Physiologically acceptable excipients are well known in the art and are disclosed, for instance in the Handbook of Pharmaceutical Excipients, sixth edition 2009, herein incorporated by reference.

The term "isomers" herein refers to structural (or constitutional) isomers (i.e. tautomers) and stereoisomers (or spatial isomers) i.e diastereoisomers and enantiomers.

DESCRIPTION OF THE INVENTION

It has now been found that benzo-N-hydroxy amide compounds having an alpha-amino acidic scaffold carrying an alpha-beta unsaturated carbonyl moiety on the amino-group show a high inhibitory activity on the proliferation of tumor cells and of staminal tumor cells. These compounds are particularly active on cancer stem cells, making them useful in the treatment of human neoplasia.

The present invention provides compounds of the formula (I):

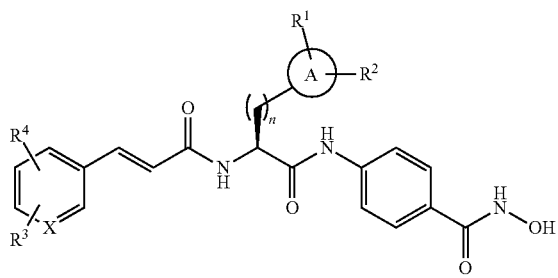

and pharmaceutically acceptable salts, isomers and prodrugs thereof,
wherein:
n is 0, 1 or 2;
A is absent or is a mono or di-carbocyclic residue, optionally partially or totally unsaturated, comprising carbon atoms and optionally one or more heteroatoms selected from N, S or O;
$R^1$ and $R^2$ are independently selected from the group comprising —H, —OH, —OMe, —CN, —NH$_2$, —NO$_2$, —Cl, —COOH, -halogen, —CF$_3$, —N(Ra)$_2$, linear or branched C$_1$-C$_4$ alkyl, aryl, arylalkyl, arylcarbonyl, alkoxy, aryloxy residue, sulphonylamino and —CH$_2$N(CH$_2$CH$_3$)$_2$;
Ra is a linear or branched C$_1$-C$_3$ alkyl residue;
X can be C or N;
$R^3$ and $R^4$ are independently selected from the group comprising —H, —OMe, —OPh, —NO$_2$, —NMe$_2$, —NH$_2$, -halogen, —CF$_3$, —N(Ra)$_2$, linear or branched C$_1$-C$_4$ alkyl, aryl, arylalkyl, arylcarbonyl, alkoxy, aryloxy residue and sulphonylamino, or $R^3$ and $R^4$ together can form a heteropentacyclic moiety (—OCH$_2$O—).

The compounds of the present invention can exist in different isomeric forms: the cis-form and the trans-form.
The preferred isomeric form is the trans-form.
The compounds of the invention contain one or more chiral centers (asymmetric carbon atoms) and may thus exist in enantiomeric and/or diastereoisomeric forms; all possible optical isomers, alone or mixed with one another, fall within the scope of the present invention.

Prodrugs of compounds of formula (I) are included in this invention. Such prodrugs are bioreversible derivatives of compounds (I). They are pharmacologically inactive derivatives, which can undergo in vivo metabolic transformation to afford an active compound included in the general formula of this invention. Many different prodrugs are known in the art [Prodrug approach: an effective solution to overcome side-effects, Patil S. J., Shirote P. J., International Journal of Medical and Pharmaceutical Sciences, 2011, 1-13; Carbamate Prodrug Concept for Hydroxamate HDAC Inhibitors, Jung, Manfred et al., ChemMedChem, 2011, 1193-1198]. Some compounds of formula (I) present one or more basic or acidic moieties, which can undergo salification by conventional chemical methods, generally treatment of the compounds with organic or inorganic acid, organic or inorganic base, or by ion-exchange chromatography. Examples of pharmaceutically acceptable salts include, but are not limited to, those deriving from inorganic acids such as hydrochloric, hydrobromic, sulfuric, phosphoric, nitric and the like, or from organic acids such as acetic, maleic, propionic, succinic, glycolic, stearic, malic, tartaric, citric, ascorbic, pamoic and the like. Further examples of pharmaceutically acceptable salts include, but are not limited to, those deriving from bases such as aluminium, ammonium, calcium, copper, ferric, lithium, magnesium, potassium, sodium, zinc and the like. Pharmaceutically acceptable salts are well known in the art. Their preparation is well described by Berg et al. in "Pharmaceutica salts", J. Pharm. Sci., 1977, 66, 1-19.

One class of preferred compounds comprises compounds of the formula (I) and pharmaceutically acceptable salts, isomers and prodrugs thereof, in which:
n is 0, 1 or 2;
A is absent or is a mono or di-carbocyclic residue, optionally partially or totally unsaturated, comprising carbon atoms and optionally one or more heteroatoms selected from N, S or O;
$R^1$ and $R^2$ are independently selected from the group comprising —H, —OH, —OMe, —CN, —NH$_2$, —NO$_2$, —Cl, —COOH and —CH$_2$N(CH$_2$CH$_3$)$_2$;
X can be C or N;
$R^3$ and $R^4$ are independently selected from the group comprising —H, —OMe, —OPh, —NO$_2$, —NMe$_2$ and —NH$_2$, or $R^3$ and $R^4$ together can form a heteropentacyclic moiety (—OCH$_2$O—).

Preferably, A is absent or is a mono or di-carbocyclic residue selected from the group comprising phenyl, naphthyl, pyridyl, indanyl, quinolyl, imidazolyl, indolyl, thiazolyl, benzothiophenyl.

Another class of more preferred compounds comprises compounds of the formula (I) and pharmaceutically acceptable salts, isomers and prodrugs thereof in which:
n is 1, X is C;
$R^1$ and $R^2$ are independently —H, —Cl or —OMe;
$R^3$ and $R^4$ are independently —H, —NMe$_2$, or $R^3$ and $R^4$ together can form a heteropentacyclic moiety (—OCH$_2$O—).

The following compounds of the formula (I) are particularly preferred:
(2S)-2-[[(E)-3-(1,3-benzodioxol-5-yl)prop-2-enoyl]amino]-N-[4-(hydroxycarbamoyl)phenyl]-3-(4-methoxyphenyl)propanamide (1D);
(2S)—N-[4-(hydroxycarbamoyl)phenyl]-3-(4-methoxyphenyl)-2-[[(E)-3-phenylprop-2-enoyl]amino]propanamide (2D);
(2S)-2-[[(E)-3-(1,3-benzodioxol-5-yl)prop-2-enoyl]amino]-N-[4-(hydroxycarbamoyl)phenyl]-3-phenyl-propanamide (4D);
(2S)—N-[4-(hydroxycarbamoyl)phenyl]-3-phenyl-2-[[(E)-3-phenyl-2-enoyl]amino]propanamide (5D);
(2S)-2-[[(E)-3-(2,5-dimethoxyphenyl)prop-2-enoyl]amino]-N-[4-(hydroxycarbamoyl)phenyl]-3-(4-hydroxyphenyl)propanamide (7D);
(E)-3-(2,5-dimethoxyphenyl)-N-[(1R)-2-[4-(hydroxycarbamoyl)anilino]-1-indan-2-yl-2-oxo-ethyl]prop-2-enamide (8D);

(2S)-2-[[(E)-3-(2,5-dimethoxyphenyl)prop-2-enoyl]amino]-N-[4-(hydroxycarbamoyl)phenyl]-4-phenyl-butanamide (9D);

(2S)-2-[[(E)-3-(2,5-dimethoxyphenyl)prop-2-enoyl]amino]-N-[4-(hydroxycarbamoyl)phenyl]-3-phenyl-propanamide (10D);

(2S)-2-[[(E)-3-(2,5-dimethoxyphenyl)prop-2-enoyl]amino]-N-[4-(hydroxycarbamoyl)phenyl]-3-(2-naphthyl)propanamide (11D);

(E)-3-(2,5-dimethoxyphenyl)-N-[2-[4-(hydroxycarbamoyl)anilino]-2-oxo-ethyl]prop-2-enamide (12D);

(2S)-2-[[(E)-3-(2,5-dimethoxyphenyl)prop-2-enoyl]amino]-N-[4-(hydroxycarbamoyl)phenyl]propanamide (13D);

(2S)-2-[[(E)-3-(2,5-dimethoxyphenyl)prop-2-enoyl]amino]-N-[4-(hydroxycarbamoyl)phenyl]-3-(3-quinolyl)propanamide (14D);

(2S)-2-[[(E)-3-(2,5-dimethoxyphenyl)prop-2-enoyl]amino]-N-[4-(hydroxycarbamoyl)phenyl]-3-(3-pyridyl)propanamide (15D);

(2S)-2-[[(E)-3-(2,5-dimethoxyphenyl)prop-2-enoyl]amino]-N-[4-(hydroxycarbamoyl)phenyl]-3-(4-nitrophenyl)propanamide (16D);

(2S)-2-[[(E)-3-(4-aminophenyl)prop-2-enoyl]amino]-N-[4-(hydroxycarbamoyl)phenyl]-3-phenyl-propanamide (17D);

(2S)-3-(4-aminophenyl)-2-[[(E)-3-(2,5-dimethoxyphenyl)prop-2-enoyl]amino]-N-[4-(hydroxycarbamoyl)phenyl]propanamide (18D);

(2S)-3-(4-cyanophenyl)-2-[[(E)-3-(2,5-dimethoxyphenyl)prop-2-enoyl]amino]-N-[4-(hydroxycarbamoyl)phenyl]propanamide (19D);

(2S)—N-[4-(hydroxycarbamoyl)phenyl]-2-[[(E)-3-(4-nitrophenyl)prop-2-enoyl]amino]-3-phenyl-propanamide (20D);

(2S)-2-[[(E)-3-(2,5-dimethoxyphenyl)prop-2-enoyl]amino]-N-[4-(hydroxycarbamoyl)phenyl]-3-(1H-imidazol-5-yl)propanamide (21D);

(2S)-2-[[(E)-3-(3,4-dimethoxyphenyl)prop-2-enoyl]amino]-N-[4-(hydroxycarbamoyl)phenyl]-3-(3-pyridyl)propanamide (22D);

(2S)-2-[[(E)-3-(3,5-dimethoxyphenyl)prop-2-enoyl]amino]-N-[4-(hydroxycarbamoyl)phenyl]-3-(3-pyridyl)propanamide (23D);

(2S)-2-[[(E)-3-(1,3-benzodioxol-5-yl)prop-2-enoyl]amino]-N-[4-(hydroxycarbamoyl)phenyl]-3-(3-pyridyl)propanamide (24D);

(2S)-2-[[(E)-3-(1,3-benzodioxol-5-yl)prop-2-enoyl]amino]-3-(benzothiophen-3-yl)-N-[4-(hydroxycarbamoyl)phenyl]propanamide (25D);

(2S)-2-[[(E)-3-(1,3-benzodioxol-5-yl)prop-2-enoyl]amino]-N-[4-(hydroxycarbamoyl)phenyl]-3-thiazol-4-yl-propanamide (26D);

(2S)-2-[[(E)-3-(1,3-benzodioxol-5-yl)prop-2-enoyl]amino]-N-[4-(hydroxycarbamoyl)phenyl]-4-phenyl-butanamide (27D);

(2S)-2-[[(E)-3-(3,4-dimethoxyphenyl)prop-2-enoyl]amino]-N-[4-(hydroxycarbamoyl)phenyl]-3-phenyl-propanamide (28D);

(2S)-2-[[(E)-3-(1,3-benzodioxol-5-yl)prop-2-enoyl]amino]-3-(4-cyanophenyl)-N-[4-(hydroxycarbamoyl)phenyl]propanamide (29D);

(2S)-2-[[(E)-3-(3,4-dimethoxyphenyl)prop-2-enoyl]amino]-N-[4-(hydroxycarbamoyl)phenyl]-3-(1H-indol-3-yl)propanamide (30D);

(2S)-2-[[(E)-3-(1,3-benzodioxol-5-yl)prop-2-enoyl]amino]-N-[4-(hydroxycarbamoyl)phenyl]-3-(1H-indol-3-yl)propanamide (31D);

(2S)-2-[[(E)-3-(1,3-benzodioxol-5-yl)prop-2-enoyl]amino]-N-[4-(hydroxycarbamoyl)phenyl]-3-(4-nitrophenyl)propanamide (32D);

(2S)-2-[[(E)-3-(1,3-benzodioxol-5-yl)prop-2-enoyl]amino]-3-(4-chlorophenyl)-N-[4-(hydroxycarbamoyl)phenyl]propanamide (33D);

(2S)-3-(4-aminophenyl)-2-[[(E)-3-(3,4-dimethoxyphenyl)prop-2-enoyl]amino]-N-[4-(hydroxycarbamoyl)phenyl]propanamide (34D);

(2S)-3-(4-aminophenyl)-2-[[(E)-3-(1,3-benzodioxol-5-yl)prop-2-enoyl]amino]-N-[4-(hydroxycarbamoyl)phenyl]propanamide (35D);

4-[(2S)-2-[[(E)-3-(1,3-benzodioxol-5-yl)prop-2-enoyl]amino]-3-[4-(hydroxycarbamoyl)anilino]-3-oxo-propyl]benzoic acid (36D);

(2S)-2-[[(E)-3-(1,3-benzodioxol-5-yl)prop-2-enoyl]amino]-3-(3,4-dichlorophenyl)-N-[4-(hydroxycarbamoyl)phenyl]propanamide (37D);

(2S)—N-[4-(hydroxycarbamoyl)phenyl]-3-(4-methoxyphenyl)-2-[[(E)-3-phenylprop-2-enoyl]amino]propanamide (38D);

(2S)-2-[[(E)-3-(4-dimethylaminophenyl)prop-2-enoyl]amino]-N-[4-(hydroxycarbamoyl)phenyl]-3-phenyl-propanamide (39D);

(2S)-2-[[(E)-3-(4-dimethylaminophenyl)prop-2-enoyl]amino]-N-[4-(hydroxycarbamoyl)phenyl]-3-(4-methoxyphenyl)propanamide; 2,2,2-trifluoroacetic acid (40D);

(E)-N-[2-[[4-(hydroxycarbamoyl)phenyl]methylamino]-2-oxo-ethyl]-3-phenyl-prop-2-enamide (41D);

(E)-3-(1,3-benzodioxol-5-yl)-N-[2-[[4-(hydroxycarbamoyl)phenyl]methylamino]-2-oxo-ethyl]prop-2-enamide (43D);

(2S)-3-[4-(diethylaminomethyl)phenyl]-N-[4-(hydroxycarbamoyl)phenyl]-2-[[(E)-3-phenylprop-2-enoyl]amino]propanamide; 2,2,2-trifluoroacetic acid (45D);

(2S)-2-[[(E)-3-(1,3-benzodioxol-5-yl)prop-2-enoyl]amino]-3-[4-(diethylaminomethyl)phenyl]-N-[4-(hydroxycarbamoyl)phenyl]propanamide; 2,2,2-trifluoroacetic acid (46D);

(2S)—N-[4-(hydroxycarbamoyl)phenyl]-3-(2-naphthyl)-2-[[(E)-3-(6-phenoxy-3-pyridyl)prop-2-enoyl]amino]propanamide (47D).

The following compounds of the formula (I) are more particularly preferred:

(2S)-2-[[(E)-3-(1,3-benzodioxol-5-yl)prop-2-enoyl]amino]-N-[4-(hydroxycarbamoyl)phenyl]-3-(4-methoxyphenyl)propanamide (1D);

(2S)—N-[4-(hydroxycarbamoyl)phenyl]-3-(4-methoxyphenyl)-2-[[(E)-3-phenylprop-2-enoyl]amino]propanamide (2D);

(2S)-2-[[(E)-3-(1,3-benzodioxol-5-yl)prop-2-enoyl]amino]-N-[4-(hydroxycarbamoyl)phenyl]-3-phenyl-propanamide (4D);

(2S)—N-[4-(hydroxycarbamoyl)phenyl]-3-phenyl-2-[[(E)-3-phenyl-2-enoyl]amino]propanamide (5D).

The compounds of the invention may be prepared using methods known to the person skilled in the art.

All starting materials, building blocks, reagents, acids, bases, solvents and catalysts used to synthesize compounds of the present invention are commercially available.

Compounds of formula (I) can be prepared both by solid phase synthesis (scheme 1) and by solution synthetic method (scheme 2). In some cases it could be necessary to synthesize the compound in a protected species and to add one or more step for the de-protection.

Reactions are monitored by HPLC or LC-MS analysis.

Final products are generally purified by preparative HPLC-MS chromatography or by SPE on reverse phase filled cartridge.

Solid Phase Synthesis

Compounds of formula (I) can be synthesised by SPS following scheme 1.

N-fmoc-4-aminobenzoic acid is loaded on hydroxylamine Wang resin after classical activation with HATU, HOAt and DIPEA. The Fmoc-deprotection is performed by treating the resin with piperidine 20% solution in DMF for 15 minutes.

A fmoc-amino acid is then coupled to the aromatic amine, after activation with HATU, HOAt and DIPEA. Another fmoc-deprotection step follows and finally the amine group is acylated by treatment of the resin with an activated cinnamic acid derivative. Cleavage of the product from the resin is obtained by treatment with TFA 50% solution in DCM.

Final products are usually purified by preparative LC-MS chromatography or by SPE on $C_{18}$ filled cartridge.

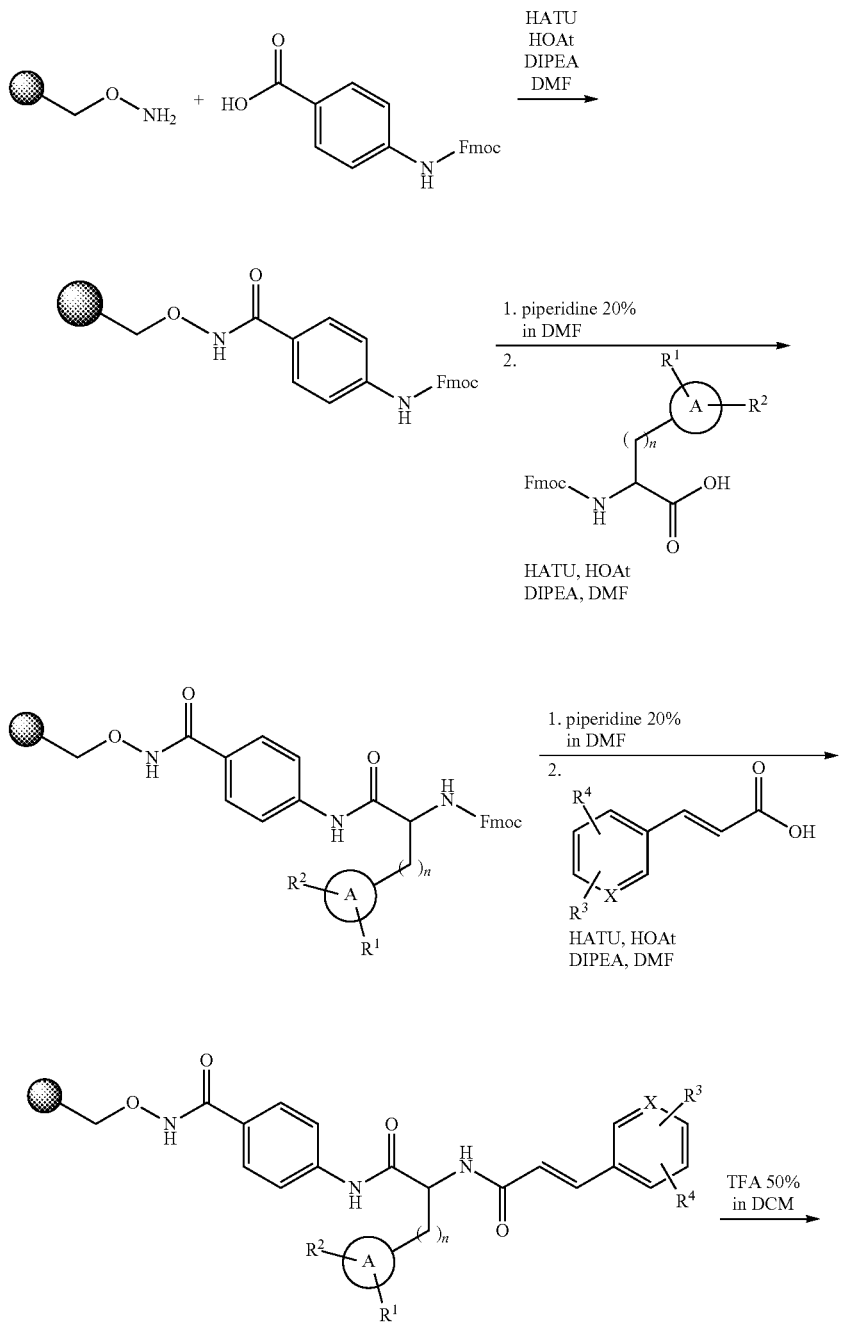

Scheme 1

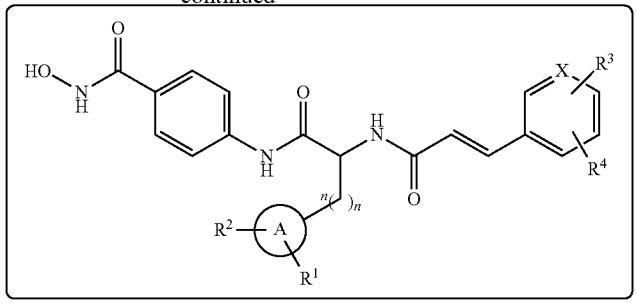

Solution Phase Synthesis

Compounds of formula (I) can also be prepared by classical solution synthesis, as shown in scheme 2. The formation of the amide can be performed using one of the method known to one of skill in the art. For example, after activation of carboxylic moiety with HATU and DIPEA, a Fmoc-amino acid is reacted with ethyl-4-aminobenzoate. The obtained compound A is deprotected by treatment with piperidine 20% in DMF and then acylated by reaction with activated cinnamic acid derivative to give the intermediate B. The final hydroxamic compound can be obtained following different synthetic route. It is possible to perform a direct hydroxylaminolysis by treatment of the ester intermediate with hydroxylamine and NaOH in methanol.

Otherwise it is possible to hydrolyse the ester function with NaOH and then to transform the obtained carboxylic acid in hydroxamic acid by reaction with hydroxylamine after activation via HATU.

In some cases it is preferably to transform the carboxylic acid in a protected form of hydroxamate, in order to perform a purification of a compound easier to handle. In this case the final compound is obtained by deprotection with a TFA solution in Methanol.

Scheme 2

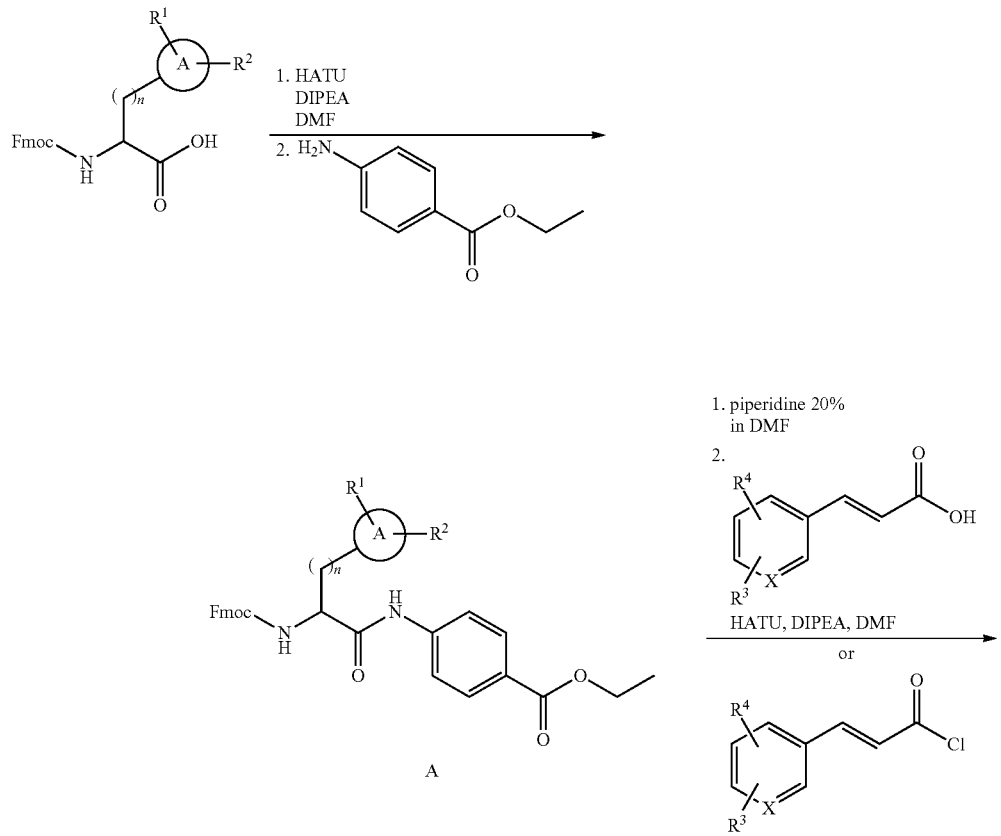

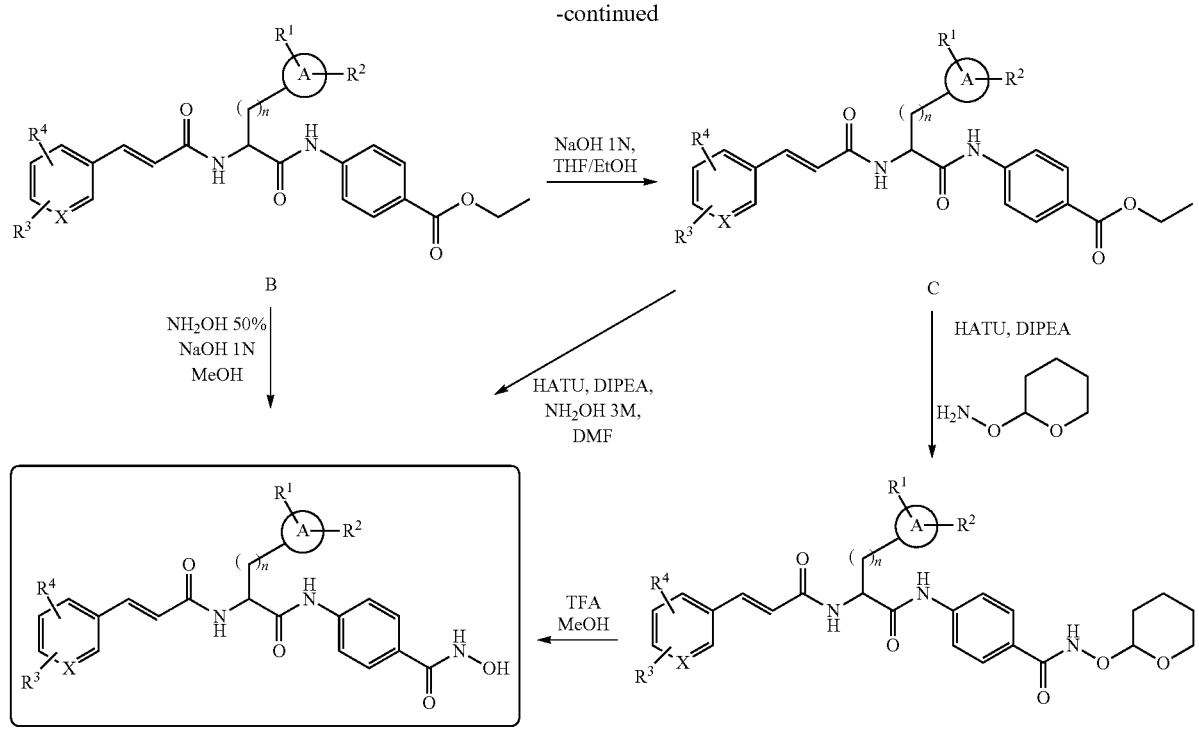

wherein A, $R^1$, $R^2$, $R^3$, $R^4$ and X have the same meanings reported above.

Preparative HPLC-MS Chromatography

The purification was performed using a Waters preparative HPLC system, equipped with a mass spectrometer detector (ZQ200). Three different methods have been used for purification, depending on the nature of $R^1$, $R^2$, $R^3$ and $R^4$ groups.

Crude product was dissolved in DMSO. The solution was filtered through a 0.45 μm PTFE membrane and injected in the preparative system. Fractions corresponding to the peak associated with the expected molecular ion ($[M+H]^+$) were collected and concentrated to dryness.

Operating Conditions:

| Column: | Waters SunFire™ Prep C18 OBD™ 5□m, 19 × 100 mm |
| --- | --- |
| Solv. A | $H_2O$ |
| Solv. B | ACN |
| Solv. C | 1% formic acid in $H_2O$ |

HPLC Method 1:

| Time (min) | Solv. A | Solv. B | Solv. C | Flow rate (ml/min) |
| --- | --- | --- | --- | --- |
| 0 | 55% | 35% | 10% | 20 |
| 20 | 45% | 45% | 10% | 20 |
| 22 | 0% | 90% | 10% | 20 |
| 24 | 0% | 90% | 10% | 20 |
| 26 | 55% | 45% | 10% | 20 |
| 30 | 55% | 45% | 10% | 20 |

HPLC Method 2:

| Time (min) | Solv. A | Solv. B | Solv. C | Flow rate (ml/min) |
| --- | --- | --- | --- | --- |
| 0 | 70% | 20% | 10% | 20 |
| 20 | 50% | 40% | 10% | 20 |
| 22 | 0% | 90% | 10% | 20 |
| 24 | 0% | 90% | 10% | 20 |
| 26 | 70% | 20% | 10% | 20 |
| 30 | 70% | 20% | 10% | 20 |

HPLC Method 3:

| Time (min) | Solv. A | Solv. B | Solv. C | Flow rate (ml/min) |
| --- | --- | --- | --- | --- |
| 0 | 75% | 15% | 10% | 20 |
| 20 | 55% | 35% | 10% | 20 |
| 22 | 0% | 90% | 10% | 20 |
| 24 | 0% | 90% | 10% | 20 |
| 26 | 75% | 15% | 10% | 20 |
| 30 | 75% | 15% | 10% | 20 |

Ms Method:

| Centroid ES+ | ionisation, |
| --- | --- |
| Scan time | 30 min, |
| m/z scan | 100-1000, |
| Cone voltage | 15 V, |
| Source temperature | 150° C., |
| Desolvation temperature | 280° C. |

Solid Phase Extraction

The purification has been performed on reverse phase pre-filled SPE cartridge (Phenomenex Strata C18-E, 55 mm, 70A).

Crude product was dissolved in DMF and loaded on the cartridge. The product was eluted with ACN/water mixtures at different ratios, depending on the nature of $R^1$, $R^2$, $R^3$ and $R^4$ groups. Eluted fractions which showed a HPLC purity area over 85% were collected and concentrated to dryness.

The compounds of the present invention showed high inhibitory activity on the proliferation of cancer stem cells in vitro, with $IC_{50}$ values of nanomolar order.

In vivo studies were also carried out, monitoring the capability of compounds to reduce tumor size and weight as described, for example, in Example 7.

These compounds may accordingly be used, alone or together with other antitumor drugs, in the prevention and/or treatment of cancer.

The compounds of the invention are preferably useful for the prevention and/or treatment of solid tumors such as colorectal cancer, lung, brain, prostate or gynecological cancers or hematologic malignancies.

The compounds of the invention are particularly active on cancer stem cells. Therefore, said compounds are preferably useful for the prevention and/or treatment of metastatic, recurrent and drug-resistant diseases.

The present invention accordingly also provides pharmaceutical compositions comprising a therapeutically effective quantity of the compounds of the formula (I) or of the pharmaceutically acceptable salts, isomers and prodrugs thereof together with at least one pharmaceutically acceptable excipient.

Such compositions may be liquid, suitable for enteral or parenteral administration, or solid, for example, in the form of capsules, tablets, coated tablets, powders or granules for oral administration, or in forms suitable for cutaneous administration, such as for example creams or ointments, or inhalatory administration.

The pharmaceutical compositions provided by the present invention may be prepared using known methods.

The following examples have the purpose of further illustrating the invention without however limiting it.

EXAMPLES

The abbreviations below are used in the following Examples:
- ACN Acetonitrile
- Boc tert-Butyloxycarbonyl
- DCM dichloromethane
- DEA diethylamine
- DIPEA N,N-diisopropylethylamine
- DMF dimethylformamide
- DMSO dimethylsulfoxide
- EtOAc ethyl acetate
- EtOH Ethanol
- Et2O diethyl ether
- ES Electrospray
- Fmoc Fluorenylmethyloxycarbonyl
- HATU O-(7-azabenzotriazol-yl-)-N,N,N',N'-tetramethyluronium hexafluorophosphste
- HOAt 1-hydroxy-7-azabenzotriazole
- HPLC high pression liquid chromatography
- LC-MS HPLC system equipped with a mass spectrometer
- MeOH methanol
- PTFE Polytetrafluoroethylene
- RT Room Temperature
- SPE solid phase extraction
- SPS solid phase synthesis
- TFA trifluoroacetic acid
- THF tetrahydrofurane Example 1 (Compound 4D)

Synthesis of (S,E)-4-(2-(3-(benzo[d][1,3]dioxol-5-yl)acrylamido)-3-phenylpropanamido)-N-hydroxy-benzamide

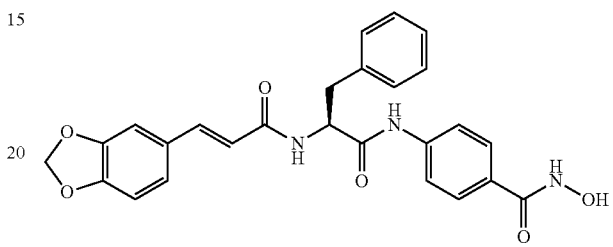

Step A: Ethyl (S)-4-(2-((((9H-fluoren-9-yl)methoxy)carbonyl)amino)-3-phenylpropanamido)benzoate

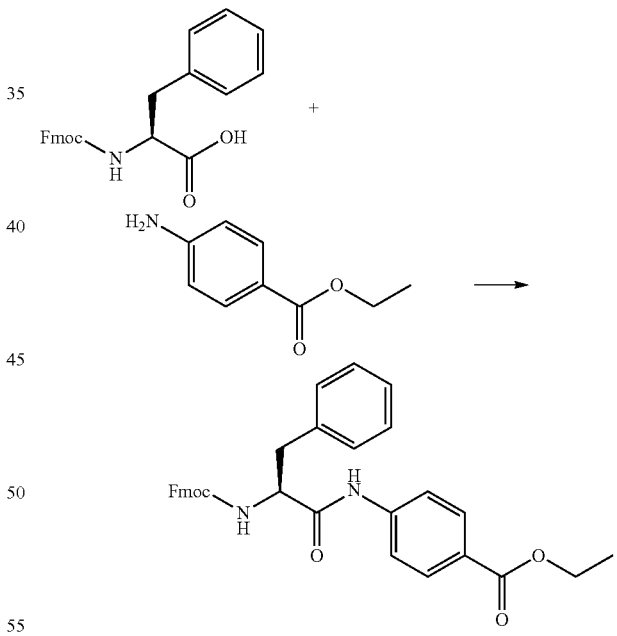

3 g of Fmoc-L-Phenylalanine (7.74 mmol, 1 eq.) were dissolved in 15 ml of DMF and the solution was cooled at 0° C. HATU (3.84 g, 1.3 eq.) and DIPEA (1.75 ml, 1.3 eq.) were added and the reaction mixture was stirred for half an hour. Ethyl 4-aminobenzoate (1.40 g, 1 eq.) was then added and the mixture was stirred at RT for 1 h. The reaction was monitored by HPLC analysis. When the reaction was complete, the solution was poured in water (150 ml). The white solid precipitated was filtered and dried. 4 g of pure product was obtained.

Step B: ethyl (S)-4-(2-amino-3-phenylpropanamido)benzoate

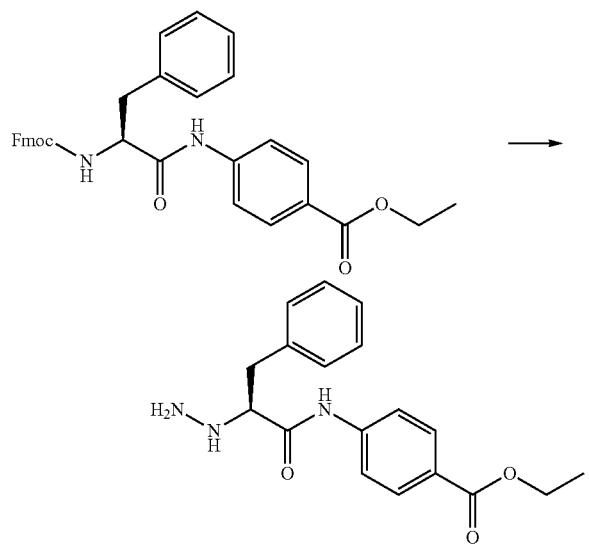

Compound obtained in step A was treated with 4.6 ml of DEA (6 eq.) in THF at RT for one night, in order to remove the Fmoc-protection. THF was removed and the residue was dissolved in n-hexane until formation of a solid. The solvent was removed and the product was washed twice with fresh n-hexane. 2.2 g of product was obtained.

Step C: ethyl (S,E)-4-(2-(3-(benzo[1,3]dioxol-5-yl)acrylamido)-3-phenylpropanamido)benzoate

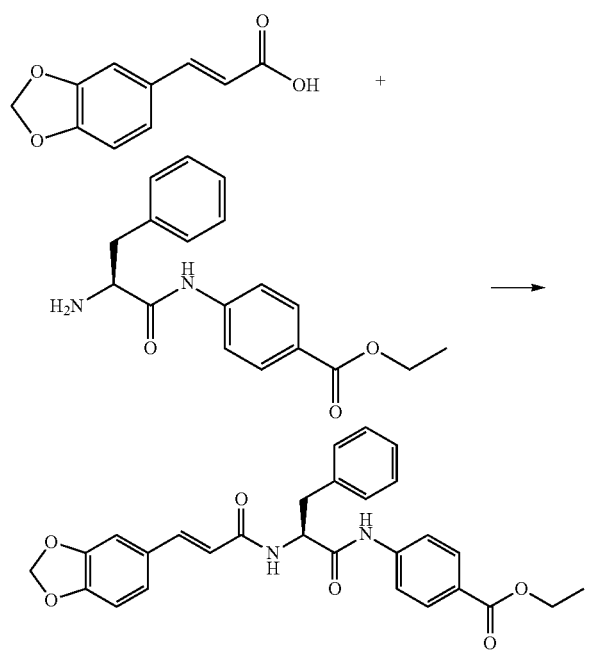

(E)-3-(1,3-benzodioxol-5-yl)prop-2-enoic acid (430 mg, 1 eq.) was dissolved in 5 ml of DMF, cooled to 0° C. and HATU (1.3 eq.) and DIPEA (1.3 eq.) were added. After 30 minutes 700 mg of compound obtained in step B was added. The reaction mixture was brought at RT and stirred for 1 h. The solution was then poured in water (50 ml) and the product was extracted with EtOAc. After acidification the solvent was evaporated and the crude product was purified on silica gel column.

Step D: (S,E)-4-(2-(3-(benzo[1,3]dioxol-5-yl)acrylamido)-3-phenylpropanamido)benzoic Acid

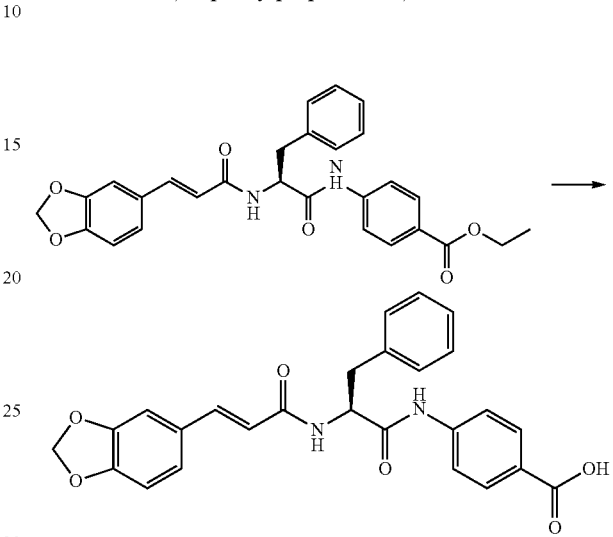

600 mg of compound obtained in step C were dissolved in 30 ml of EtOH/THF 1:2. NaOH 1N (3 eq.) was added to the solution and the reaction mixture was stirred at reflux for 4 h. Solvents were removed and the crude was dissolved in water. The solution was acidified with HCl 6N and precipitation of product was observed. The filtered solid was suspended in Et$_2$O and filtered.

Step E: (S,E)-4-(2-(3-(benzo[d][1,3]dioxol-5-yl)acrylamido)-3-phenylpropanamido)-N-hydroxybenzamide

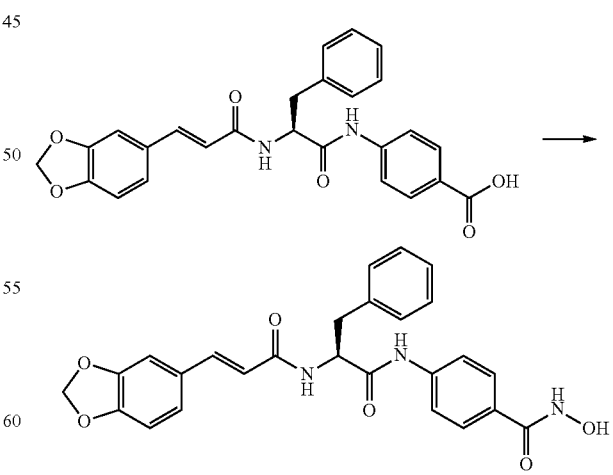

400 mg of compound obtained in step D (1 eq.) were dissolved in 2.5 ml of DMF. After cooling in ice bath, HATU (1.3 eq.) and DIPEA (1.3 eq.) were added and the mixture was stirred for 1 h. Finally a solution of NH$_2$OH 3M in DMF (3 eq.) was added and the reaction mixture was stirred at RT for 4 h. the mixture was then poured into water and the precipitated solid was filtered and suspended in dioxane and the mixture was stirred and warmed. The final product was obtained by filtration.

Example 2 (Compound 5D)

Synthesis of (S)-4-(2-cinnamamido-3-phenylpropanamido)-N-hydroxybenzamide

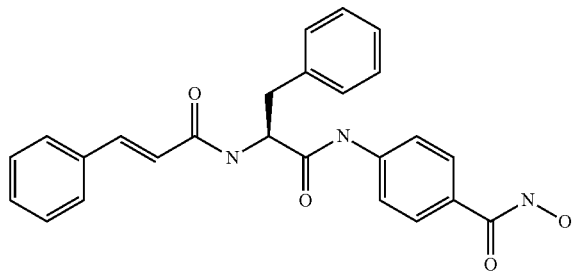

Step A: Ethyl (S)-4-(2-((((9H-fluoren-9-yl)methoxy)carbonyl)amino)-3-phenylpropanamido)benzoate

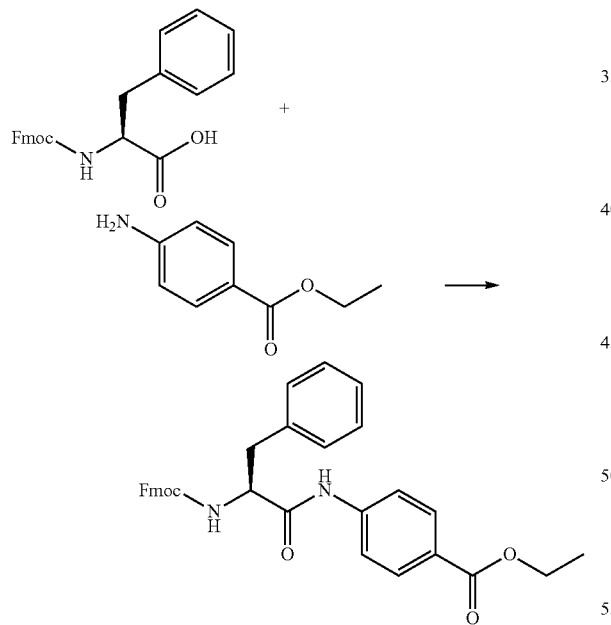

3 g of Fmoc-L-Phenylalanine (7.74 mmol, 1 eq.) were dissolved in 15 ml of DMF and the solution was cooled at 0° C. HATU (3.84 g, 1.3 eq.) and DIPEA (1.75 ml, 1.3 eq.) were added and the reaction mixture was stirred for half an hour. Ethyl 4-aminobenzoate (1.40 g, 1 eq.) was then added and the mixture was stirred at RT for 1 h. The reaction was monitored by HPLC analysis. When the reaction was complete, the solution was poured in water (150 ml). The precipitated white solid was filtered and dried. 4 g of pure product was obtained.

Step B: ethyl (S)-4-(2-amino-3-phenylpropanamido)benzoate

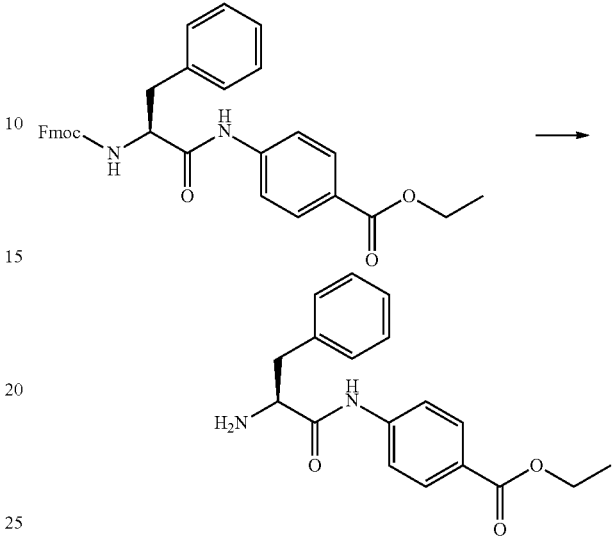

Compound obtained in step A was treated with 4.6 ml of DEA (6 eq.) in THF at RT for one night, in order to remove the Fmoc-protection. THF was removed and the residue was dissolved in n-hexane until formation of a solid. The solvent was removed and the product was washed twice with fresh n-hexane. 2.2 g of product was obtained.

Step C: ethyl (S)-4-(2-cinnamamido-3-phenylpropanamido)benzoate

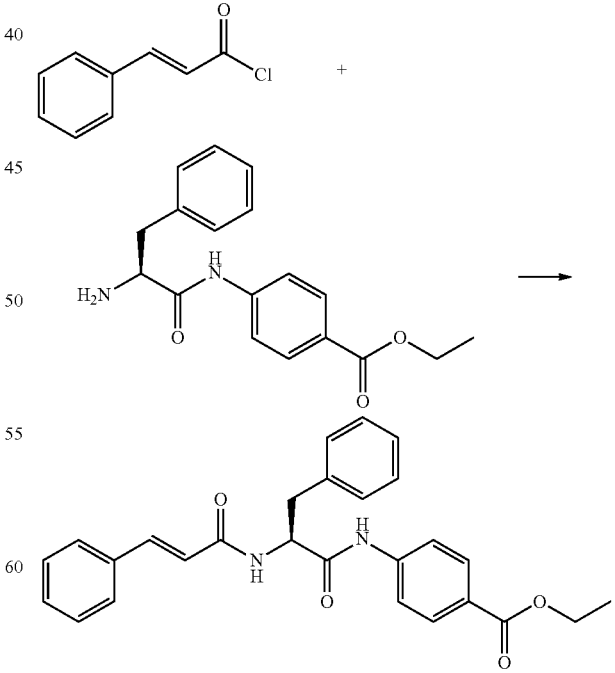

900 mg of product obtained in step B (1 eq.) were dissolved in DCM (25 ml) and the solution was cooled at 0°

C. TEA was added (1 eq.). Finally a solution of cinnamoyl chloride was added. The reaction mixture was stirred at room temperature for 1 h. After the reaction was complete, the solution was washed with water, HCl 1N and NaHCO$_3$ 5% in water. The organic phase was dried with CaCl$_2$, filtered and evaporated. The crude was purified on silica gel column using a mixture of toluene/EtOH as mobile phase.

Step D:
(S)-4-(2-cinnamamido-3-phenylpropanamido)benzoic Acid

Step E: 4-((S)-2-cinnamamido-3-phenylpropanamido)-N-((tetrahydro-2H-pyran-2-yl)oxy)benzamide

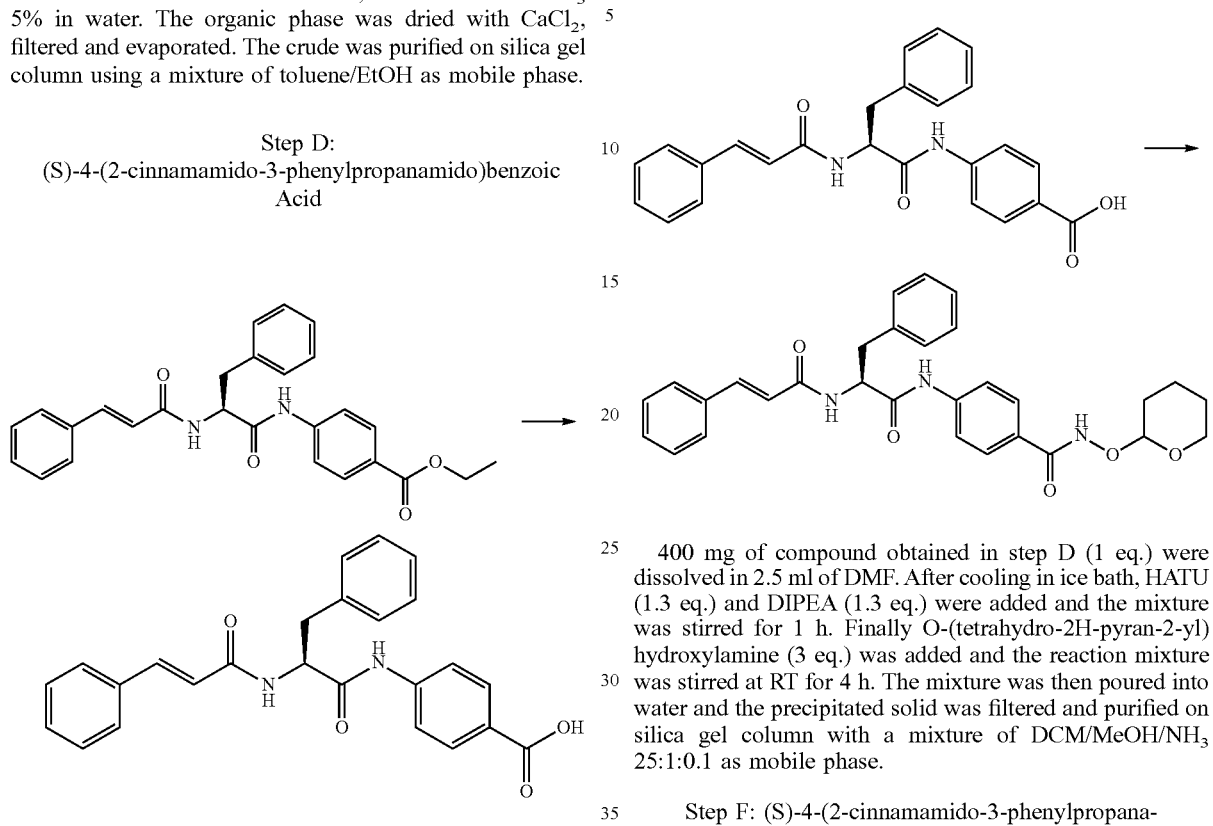

400 mg of compound obtained in step D (1 eq.) were dissolved in 2.5 ml of DMF. After cooling in ice bath, HATU (1.3 eq.) and DIPEA (1.3 eq.) were added and the mixture was stirred for 1 h. Finally O-(tetrahydro-2H-pyran-2-yl) hydroxylamine (3 eq.) was added and the reaction mixture was stirred at RT for 4 h. The mixture was then poured into water and the precipitated solid was filtered and purified on silica gel column with a mixture of DCM/MeOH/NH$_3$ 25:1:0.1 as mobile phase.

Step F: (S)-4-(2-cinnamamido-3-phenylpropanamido)-N-hydroxybenzamide

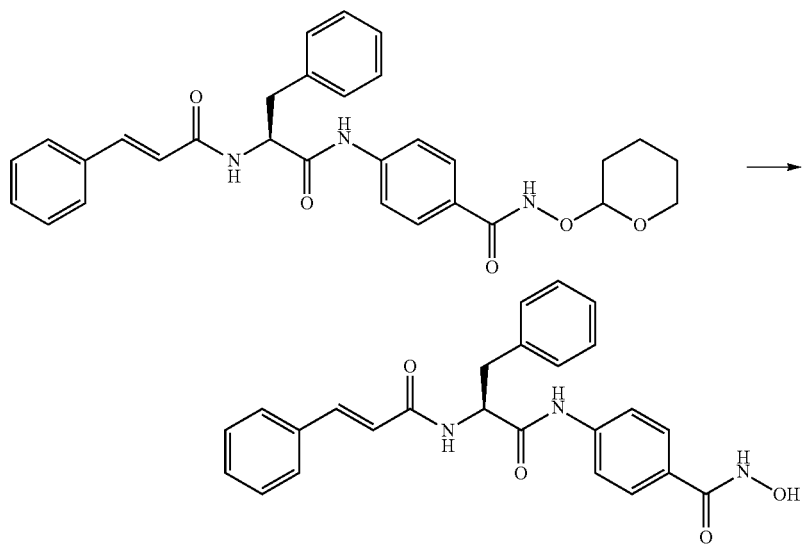

Ethyl (S)-4-(2-cinnamamido-3-phenylpropanamido)benzoate obtained in step C (400 mg, 1 eq.) was dissolved in a mixture of THF/EtOH and treated with NaOH 1N (3 eq.) for 1 h. Solvent was removed and crude was dissolved in water. Solution was acidified with conc. HCl. A solid is formed, filtered and used for the next step.

Compound obtained in step E (200 mg, 1 eq.) was dissolved in MeOH (50 ml) and treated with TFA (1.5 ml). The reaction mixture was stirred at RT overnight. The solvent and the exceeding TFA were removed by evaporation and the crude was suspended in Et$_2$O and filtered. 120 mg of pure product were obtained.

Example 3 (Compound 5DZ)

Synthesis of (S,Z)—N-hydroxy-4-(3-phenyl-2-(3-phenylacrylamido)propanamido)benzamide

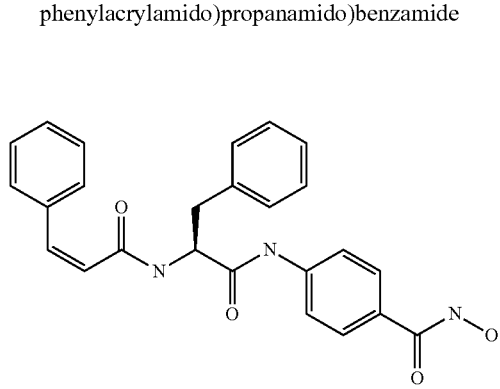

Step A: Ethyl (S)-4-(2-((((9H-fluoren-9-yl)methoxy)carbonyl)amino)-3-phenylpropanamido)benzoate

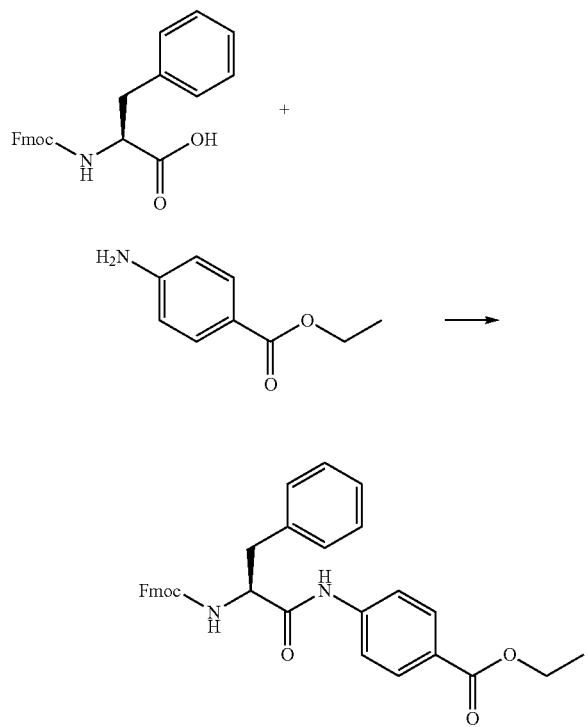

3 g of Fmoc-L-Phenylalanine (7.74 mmol, 1 eq.) were dissolved in 15 ml of DMF and the solution was cooled at 0° C. HATU (3.84 g, 1.3 eq.) and DIPEA (1.75 ml, 1.3 eq.) were added and the reaction mixture was stirred for half an hour. Ethyl 4-aminobenzoate (1.40 g, 1 eq.) was then added and the mixture was stirred at RT for 1 h. The reaction was monitored by HPLC analysis. When the reaction was complete, the solution was poured in water (150 ml).

The precipitated white solid was filtered and dried. 4 g of pure product was obtained.

Step B: ethyl (S)-4-(2-amino-3-phenylpropanamido)benzoate

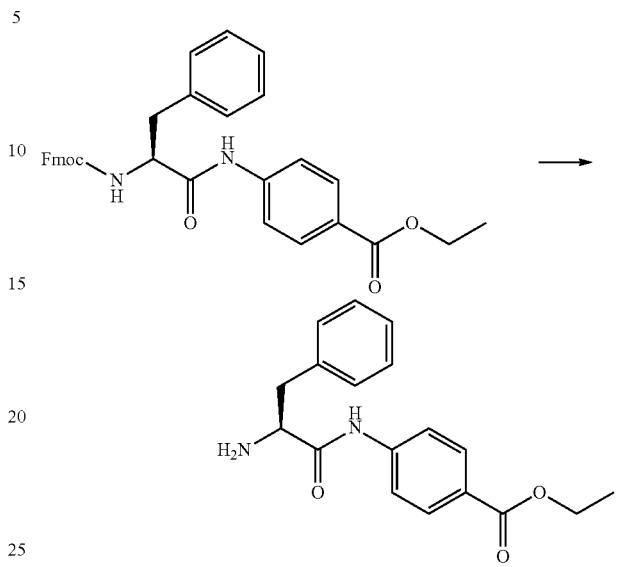

Compound obtained in step A was treated with 4.6 ml of DEA (6 eq.) in THF at RT overnight, in order to remove the Fmoc-protection. THF was removed and the residue was dissolved in n-hexane until formation of a solid. The solvent was removed and the product was washed twice with fresh n-hexane. 2.2 g of product was obtained.

Step C: ethyl (S,Z)-4-(3-phenyl-2-(3-phenylacrylamido)propanamido)benzoate

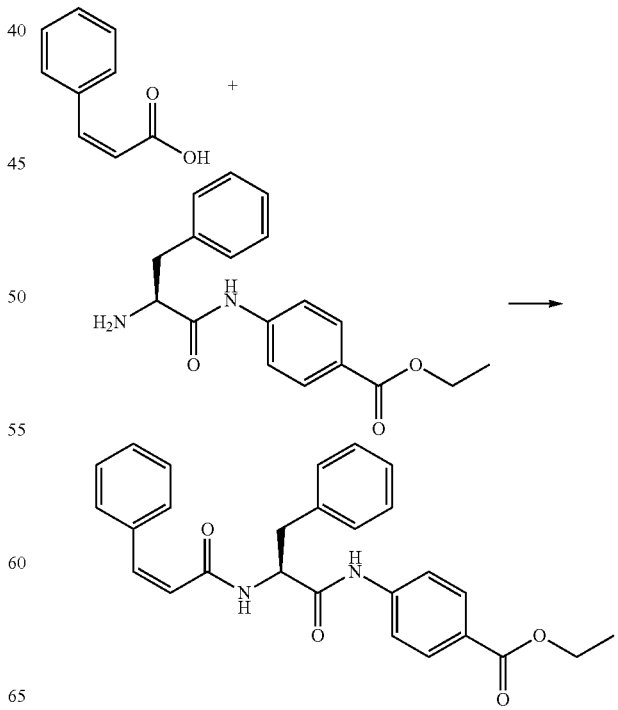

(Z)-3-phenylacrylic acid (1 eq.) was dissolved in 5 ml of DMF and the solution was cooled at 0° C. HATU (1.3 eq.) and DIPEA (1.3 eq.) were added and the reaction mixture was stirred for one hour. Ethyl (S)-4-(2-amino-3-phenylpropanamido)benzoate (1 eq.) obtained in step B was then added and the mixture was stirred at RT overnight. The reaction was monitored by HPLC analysis. When the reaction was complete, the solution was poured in water. Crude product was extracted with EtOAc and purified on silica gel column, using a mixture of toluene/EtOAC 6:4 as mobile phase.

Step D: (S,Z)-4-(3-phenyl-2-(3-phenylacrylamido)propanamido)benzoic acid

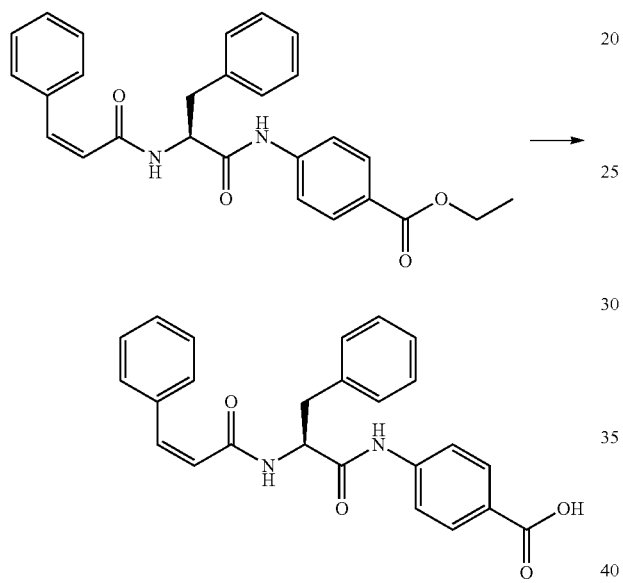

Ethyl (S,Z)-4-(3-phenyl-2-(3-phenylacrylamido)propanamido)benzoate obtained in step C (250 mg, 1 eq.) was dissolved in a mixture of THF/EtOH and treated with NaOH 1N (3 eq.) for 24 h. Solvent was removed and crude was dissolved in water. Crude product was purified by silica gel column, eluting with a mixture of Toluene/EtOAc.

Step E: 4-((S)-3-phenyl-2-((Z)-3-phenylacrylamido)propanamido)-N-((tetrahydro-2H-pyran-2-yl)oxy)benzamide

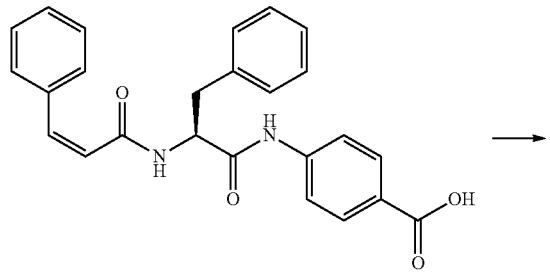

-continued

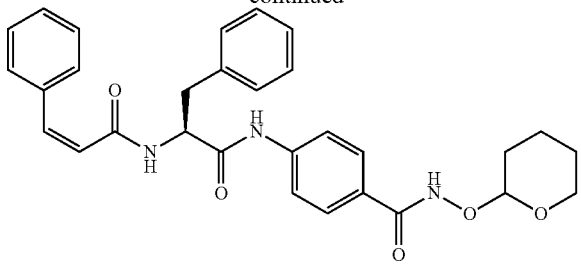

200 mg of compound obtained in step D (1 eq.) were dissolved in 1 ml of DMF. After cooling in ice bath, HATU (1.3 eq.) and DIPEA (1.3 eq.) were added and the mixture was stirred for 1 h. Finally O-(tetrahydro-2H-pyran-2-yl)hydroxylamine (1 eq.) was added and the reaction mixture was stirred at RT for 4 h. The mixture was then poured into water and the precipitated solid was filtered and purified on silica gel column with a mixture of EtOAc/Toluene 7:3 as mobile phase.

Step F: (S,Z)—N-hydroxy-4-(3-phenyl-2-(3-phenylacrylamido)propanamido)benzamide

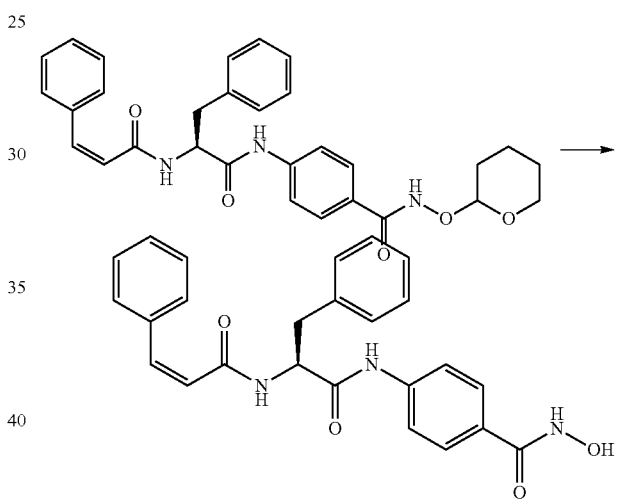

Compound obtained in step E (110 mg, 1 eq.) was dissolved in MeOH (25 ml) and treated with TFA (1 ml). The reaction mixture was stirred at RT for 4 hours. The solvent and the exceeding TFA were removed by evaporation and the crude was suspended in Et$_2$O and filtered. 80 mg of pure product were obtained.

Example 4 (Compound 1D)

Synthesis of (S,E)-4-(2-(3-(benzo[1,3]dioxol-5-yl)acrylamido)-3-(4-methoxyphenyl)propanamido)-N-hydroxybenzamide

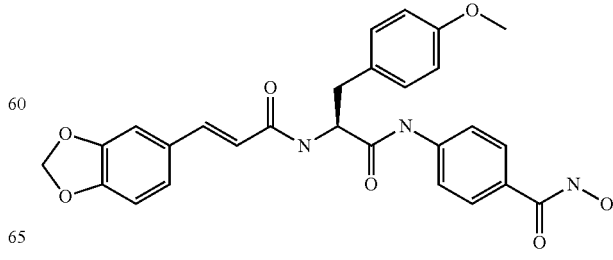

Step A: Ethyl (S)-4-(2-((((9H-fluoren-9-yl)methoxy) carbonyl)amino)-3-phenylpropanamido)benzoate

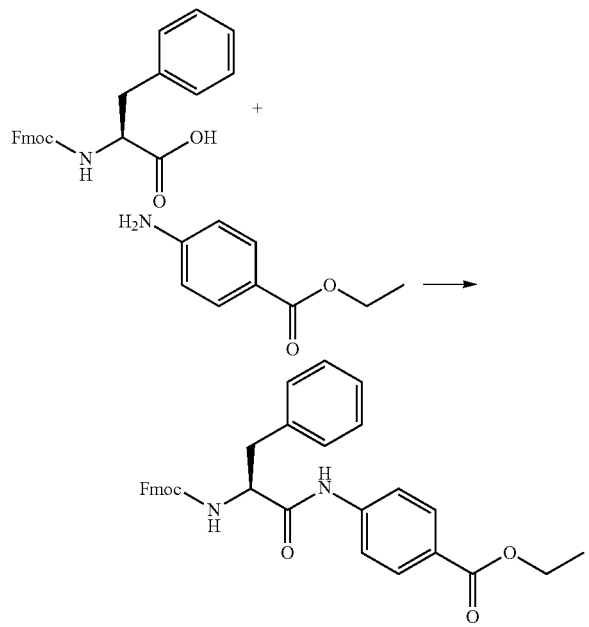

3 g of Fmoc-L-Phenylalanine (7.74 mmol, 1 eq.) were dissolved in 15 ml of DMF and the solution was cooled at 0° C. HATU (3.84 g, 1.3 eq.) and DIPEA (1.75 ml, 1.3 eq.) were added and the reaction mixture was stirred for half an hour. Ethyl 4-aminobenzoate (1.40 g, 1 eq.) was then added and the mixture was stirred at RT for 1 h. The reaction was monitored by HPLC analysis. When the reaction was complete, the solution was poured in water (150 ml). The precipitated white solid was filtered and dried. 4 g of pure product was obtained.

Step B: ethyl (S)-4-(2-amino-3-phenylpropanamido)benzoate

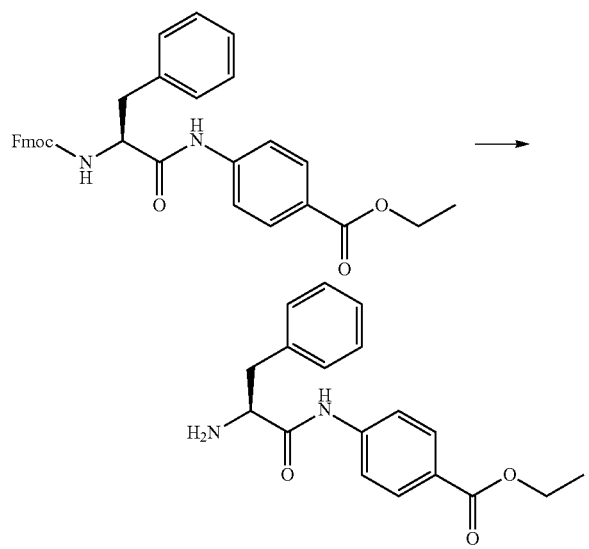

Compound obtained in step A was treated with 4.6 ml of DEA (6 eq.) in THF at RT overnight, in order to remove the Fmoc-protection. THF was removed and the residue was dissolved in n-hexane until formation of a solid. The solvent was removed and the product was washed twice with fresh n-hexane. 2.2 g of product were obtained.

Step C: ethyl (S,E)-4-(2-(3-(benzo[1,3]dioxol-5-yl)acrylamido)-3-phenylpropanamido)benzoate

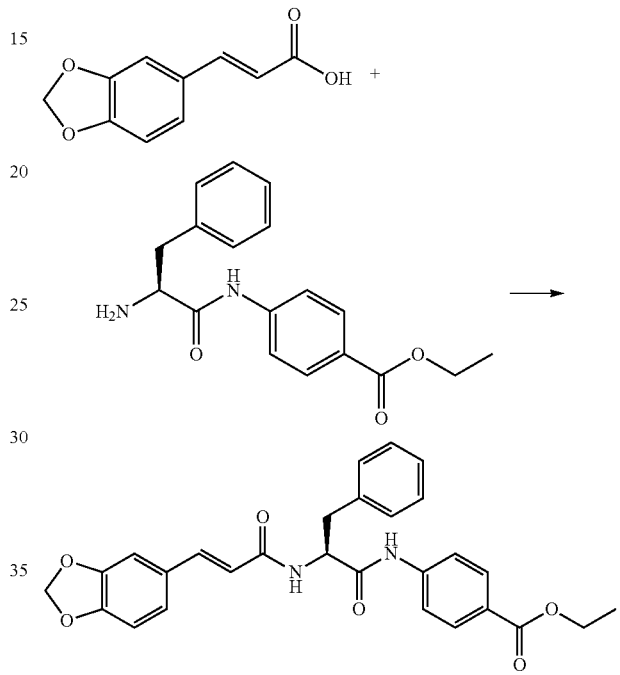

(E)-3-(1,3-benzodioxol-5-yl)prop-2-enoic acid (430 mg, 1 eq.) was dissolved in 5 ml of DMF, cooled to 0° C. and reacted with HATU (1.3 eq.) and DIPEA (1.3 eq.). After 30 minutes 700 mg of compound obtained in step B was added. The reaction mixture was brought at RT and stirred for 1 h. The solution was then poured in water (50 ml) and the product was extracted with EtOAc. After acidification the solvent was evaporated and the crude product was purified on silica gel column.

Step D: (S,E)-4-(2-(3-(benzo[1,3]dioxol-5-yl)acrylamido)-3-(4-methoxyphenyl)propanamido)-N-hydroxybenzamide

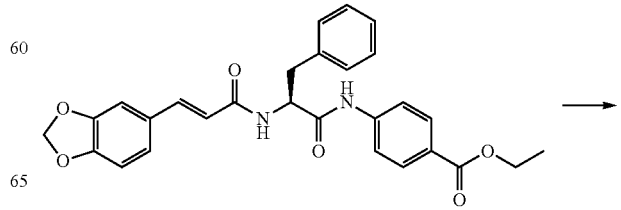

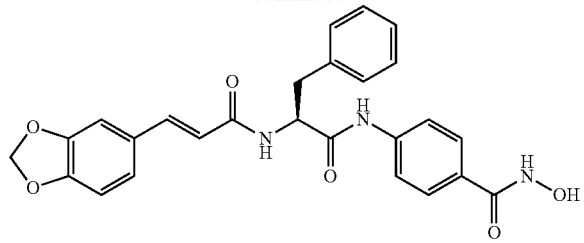 [SMILES: O=C(/C=C/c1ccc2c(c1)OCO2)N[C@@H](Cc1ccccc1)C(=O)Nc1ccc(C(=O)NO)cc1]

A solution of compound obtained in step D in MeOH was cooled in ice bath. A solution of hydroxylamine 50% in water (15 eq.) and NaOH 1N (10 eq.) were added and the reaction mixture was stirred at RT for 1 h. The solution was then neutralised with HCl 1N. A precipitation was observed. The pure product was obtained by simple filtration.

Example 5 (Compound 7D)

Synthesis of (S,E)-4-(2-(3-(2,5-dimethoxyphenyl)acrylamido)-3-(4-hydroxyphenyl)propanamido)-N-hydroxybenzamide

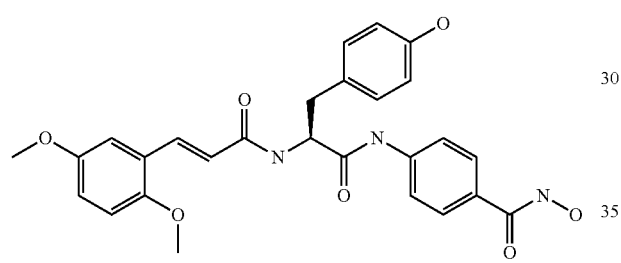

Step A: loading of (9H-fluoren-9-yl)methyl (4-(hydroxycarbamoyl)phenyl)carbamate on Hydroxylamine Wang Resin

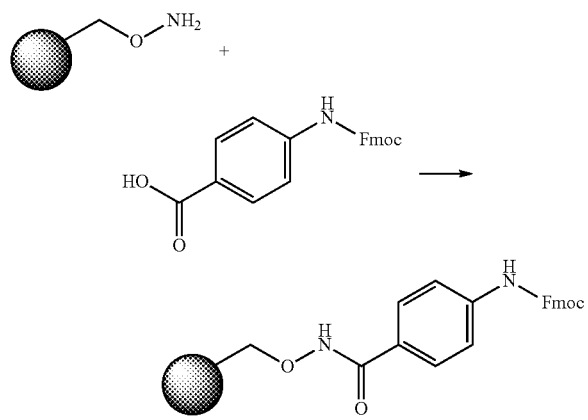

The reaction was performed in an empty SPE plastic filter tube, using an Activotec PLS 4×6 Organic Synthesizer.

After swelling of the resin with DCM and DMF, a solution of 4-((((9H-fluoren-9-yl)methoxy)carbonyl)amino)benzoic acid (4 eq.), HATU (4 eq.), HOAt (4 eq.) and DIPEA (8 eq.) in DMF was added. The reaction mixture was shaken at RT overnight. The resin was then filtered and washed with DMF and DCM.

Step B: First Coupling

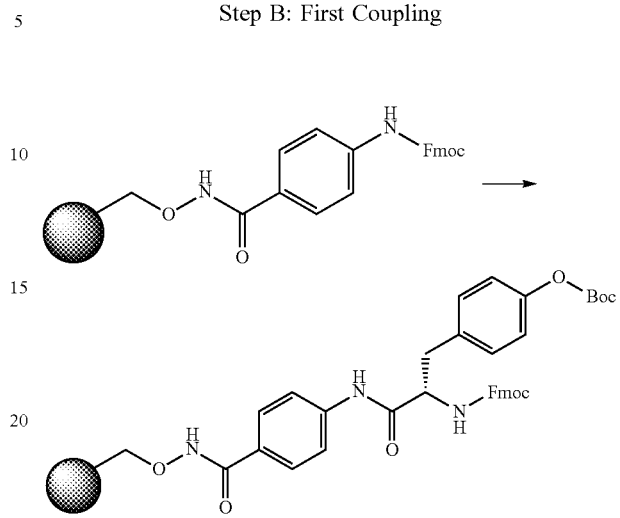

Resin from step A (200 mg, 1 eq.) was swelled in DMF, then filtered. Fmoc-deprotection was carried out by a double treatment of the resin with a solution of piperidine 20% in DMF for 30 minutes. The solution was filtered off and the resin was washed with DMF. A solution of (S)-2-((((9H-fluoren-9-yl)methoxy)carbonyl)amino)-3-(4-((tert-butoxycarbonyl)oxy)phenyl)propanoic acid (4 eq.), HATU (4 eq.), HOAt (4 eq.) and DIPEA (8 eq.) in DMF was added to the resin. The reaction mixture was shaken at RT overnight. The resin was filtered and washed with DMF and DCM.

Step C: Second Coupling

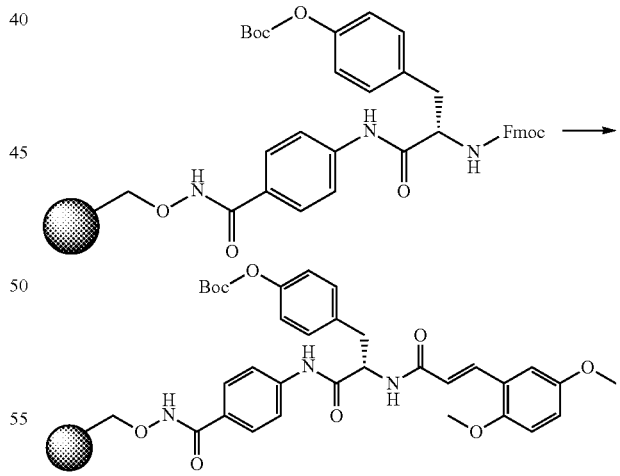

Resin from step B (1 eq.) was swelled in DMF, then filtered. Fmoc-deprotection was performed by a double treatment of the resin with a solution of piperidine 20% in DMF for 30 minutes. The solution was filtered off and the resin was washed with DMF. A solution of (E)-3-(2,5-dimethoxyphenyl)acrylic acid (4 eq.), HATU (4 eq.), HOAt (4 eq.) and DIPEA (8 eq.) in DMF was added to the resin. The reaction mixture was shaken at RT overnight. The resin was filtered and washed with DMF and DCM.

Step D: Cleavage
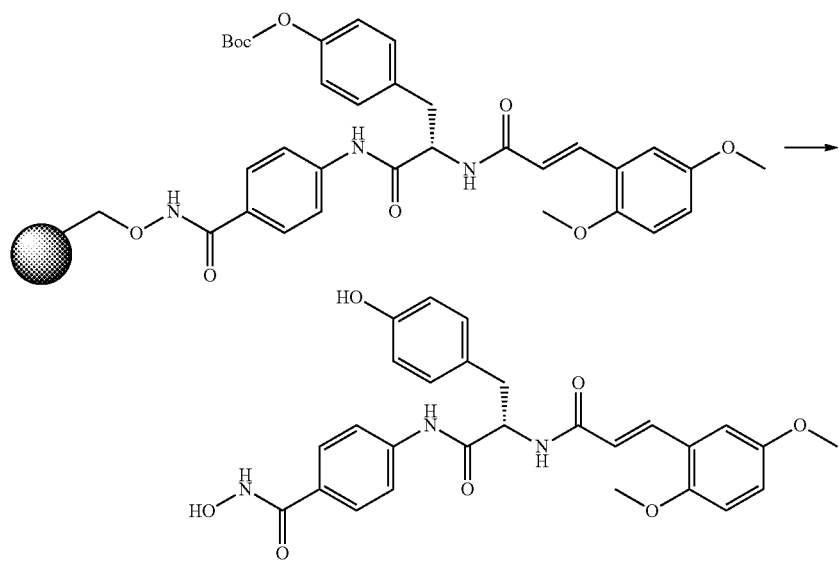
Cleavage of the product from the resin was obtained by treatment with TFA 50% in DCM at RT for 30 minutes. During this step the Boc-protection was also removed.
Crude was purified on SPE cartridge.
Example 6
The following compounds were prepared using the procedure described in example 5:
Compound 2D
Compound 8D
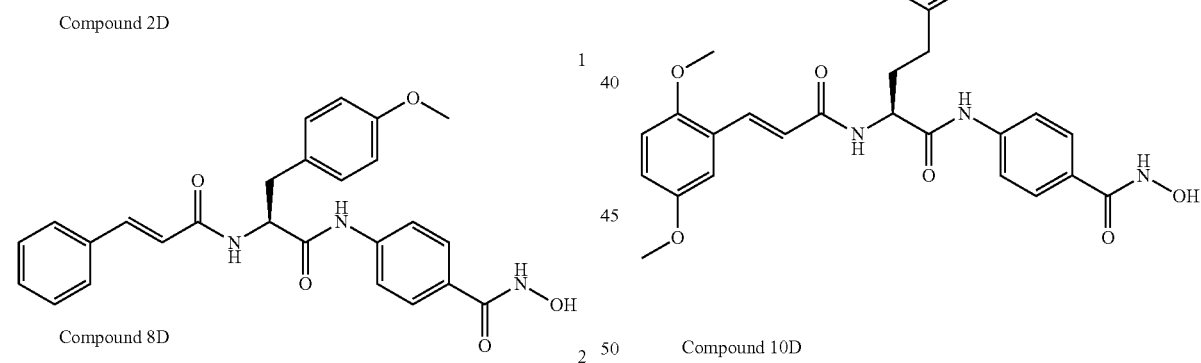
Compound 9D
Compound 10D
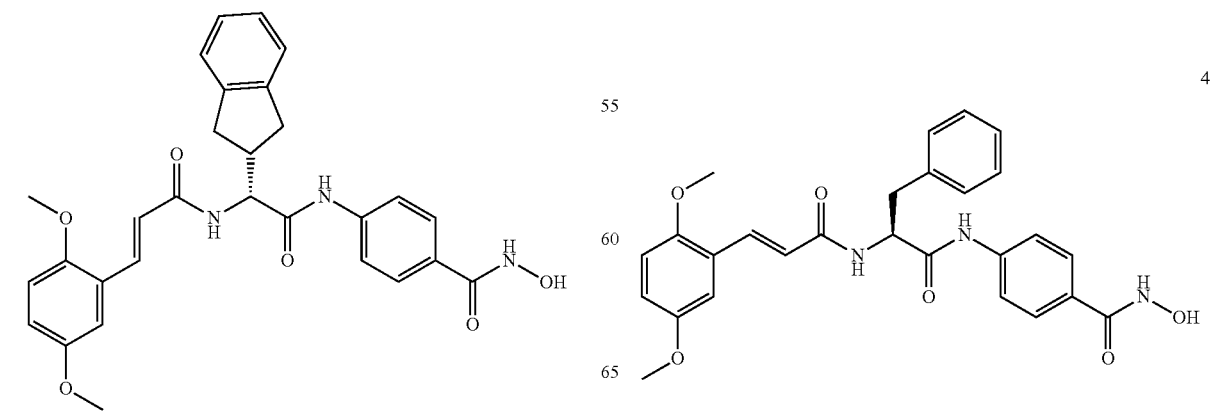

Compound 11D
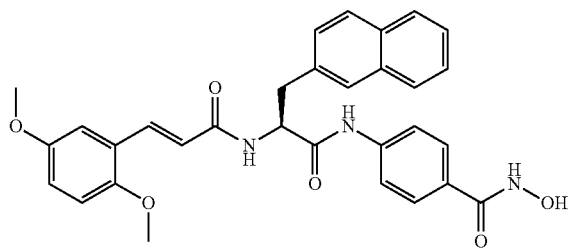
Compound 12D
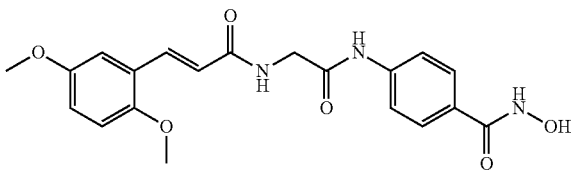
Compound 13D
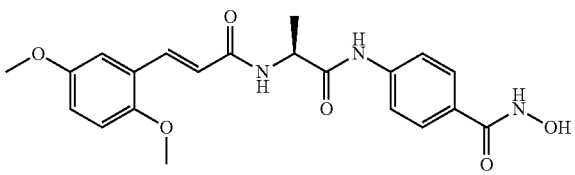
Compound 14D
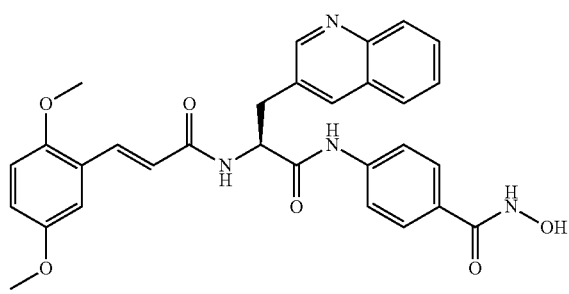
Compound 15D
Compound 16D
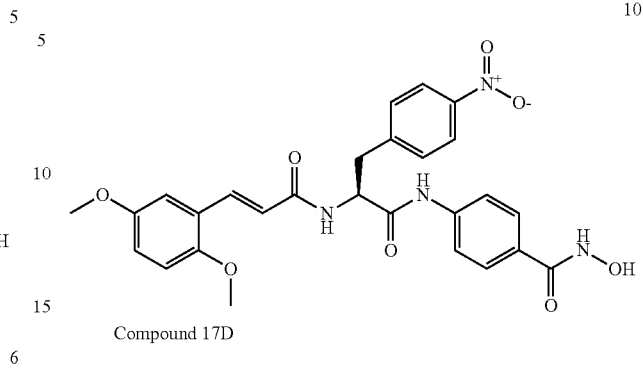
Compound 17D
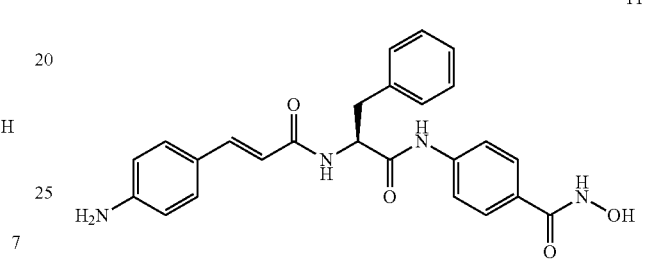
Compound 18D
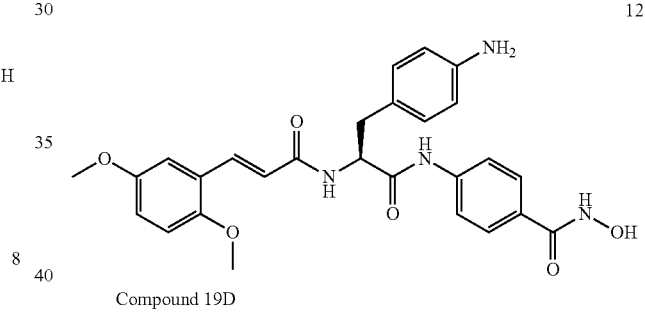
Compound 19D
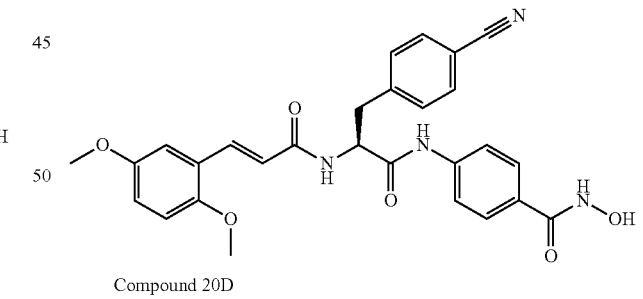
Compound 20D
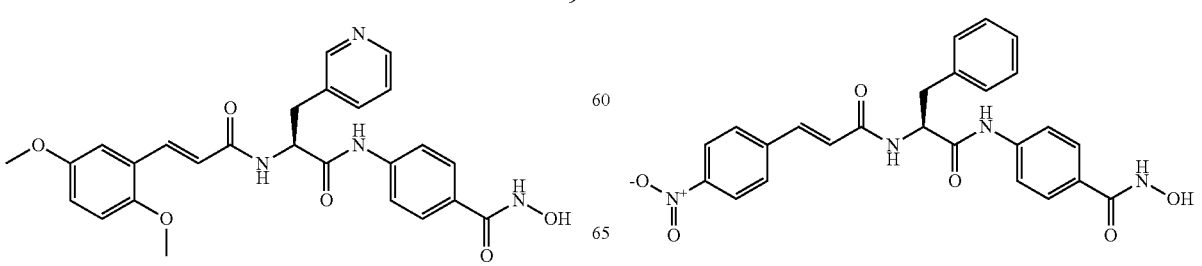

Compound 21D
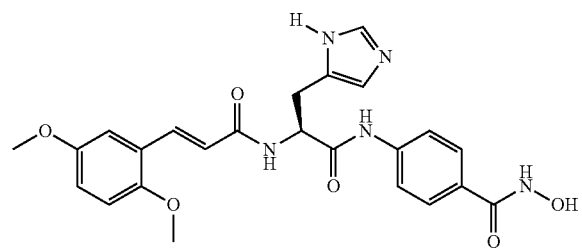
Compound 22D
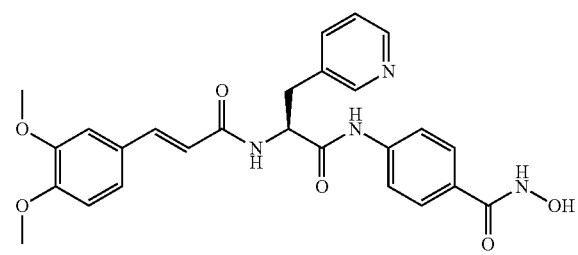
Compound 23D
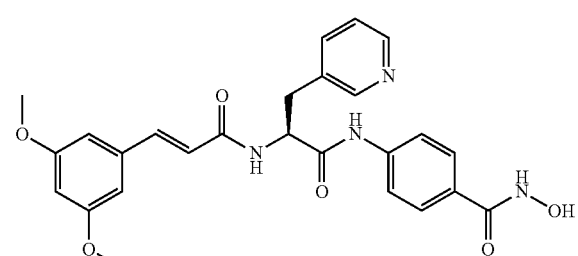
Compound 24D
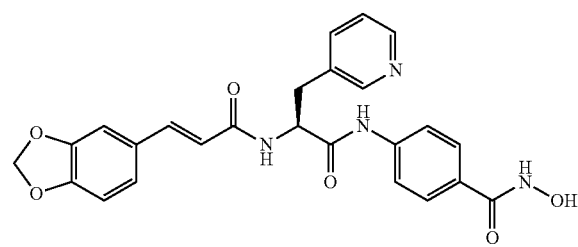
Compound 25D
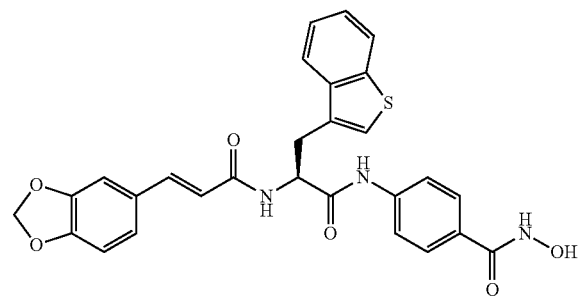
Compound 26D
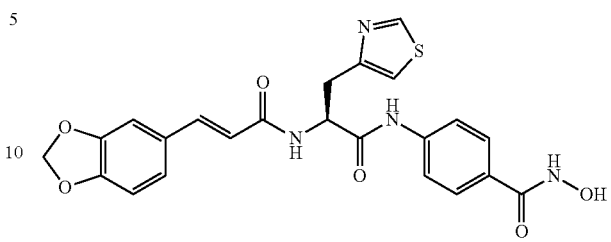
Compound 27D
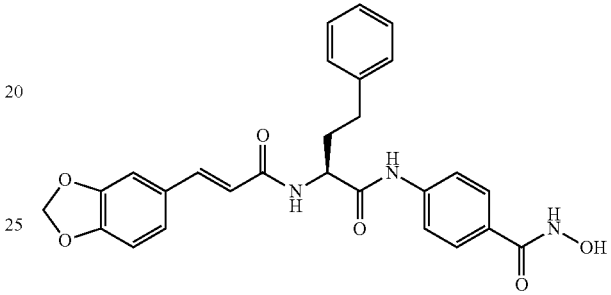
Compound 28D
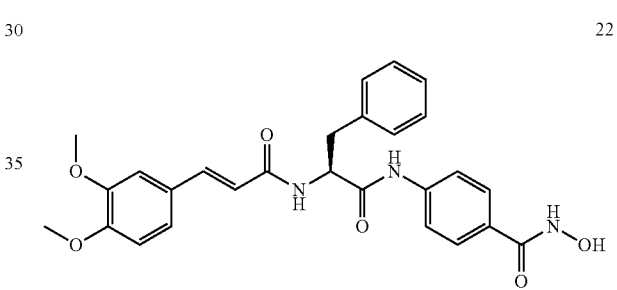
Compound 29D
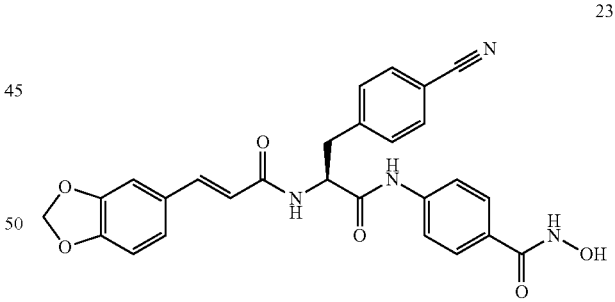
Compound 30D
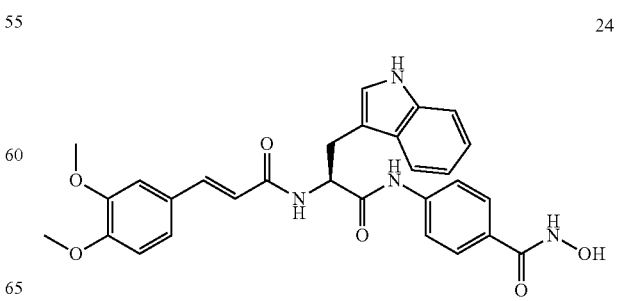

Compound 31D
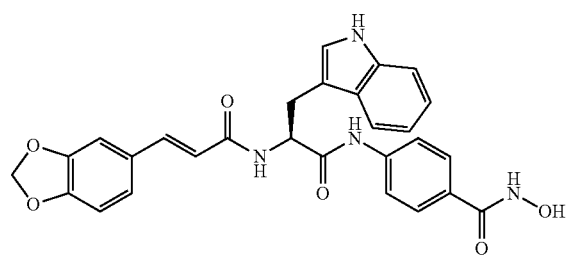
Compound 32D
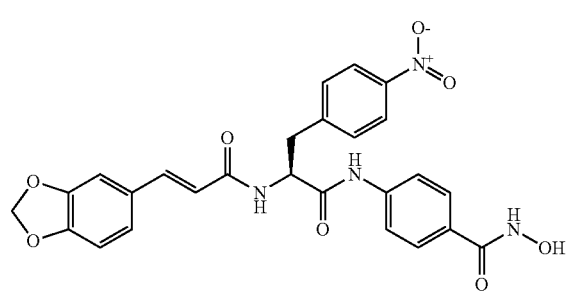
Compound 33D
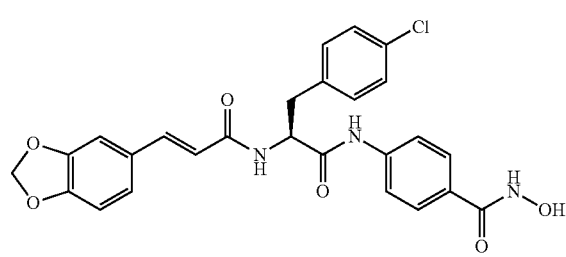
Compound 34D
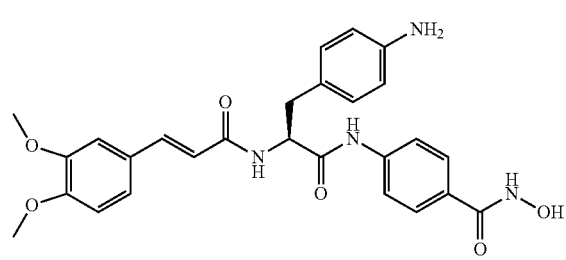
Compound 35D
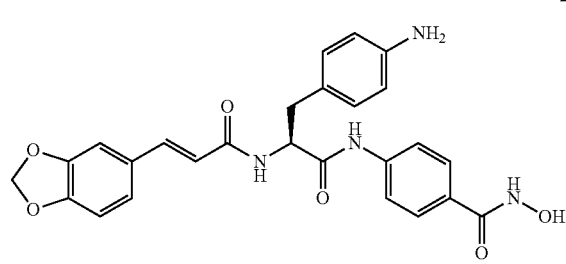
Compound 36D
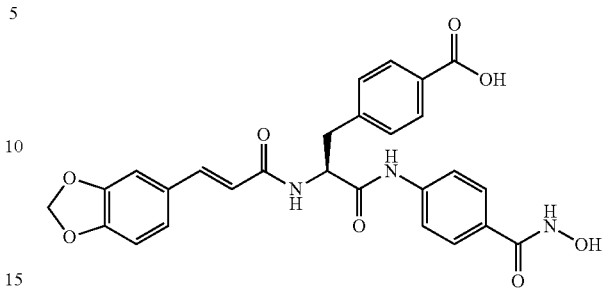
Compound 37D
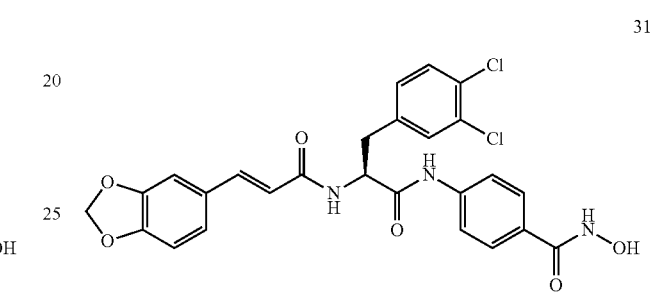
Compound 38D
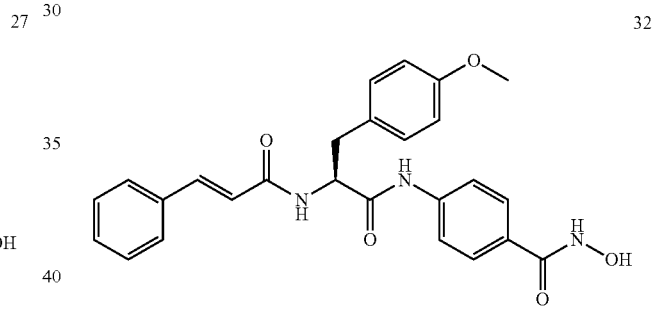
Compound 39D
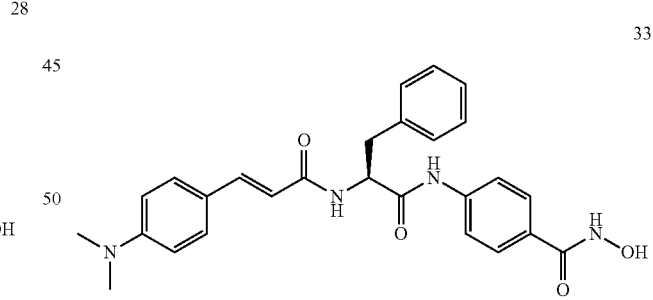
Compound 40D
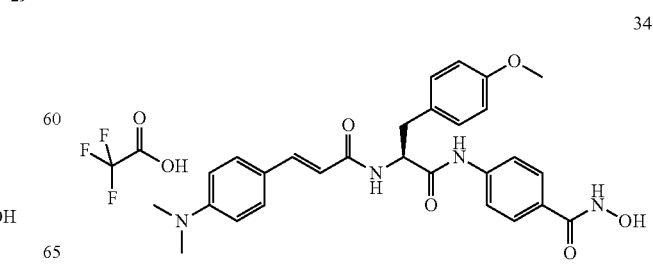

Compound 41D

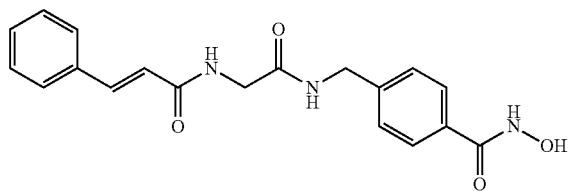

Compound 43D

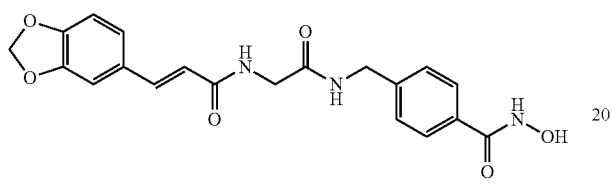

Compound 45D

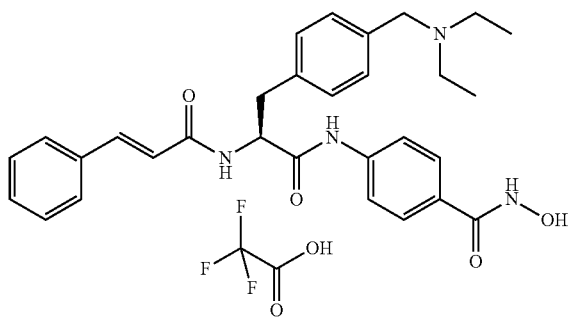

Compound 46D

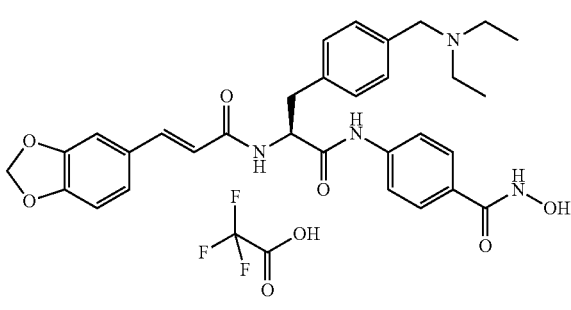

Compound 47D

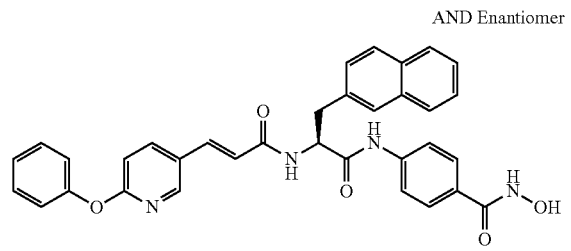

Example 7

Cytotoxicity Activity In Vitro

The compounds of the present invention are small molecules of formula (I), characterised by the presence of a metal chelating moiety, the benzohydroxamate, an α-aminoacidic N-acylated central core and an α,β-unsaturation at the acyl-moiety. This particular structural feature seems responsible for the high inhibitory activity on cancer stem cell lines and on HCT116 cells (ATCC CCL-247), a human colorectal carcinoma cell line widely used in cancer biology both in vitro and in vivo (Botchkina Cancer Genom Proteom 6, 19-30, 2009; Yeung PNAS 107, 3722-3727, 2010).

The cytotoxicity activity was evaluated as follows:

Pre-B leukemia cell line 697 was seeded at $2 \times 10^5$ c/well;

Colon carcinoma cell lines HCT116, HT29 and COLO2015 were seeded at $4 \times 10^3$, $4 \times 10^3$ and $10 \times 10^3$ c/well respectively;

Primary human kidney cells were seeded at $1.5 \times 10^3$ and $6.5 \times 10^3$ in two separate experiments;

Human PBMC were seeded at $5 \times 10^5$ c/well;

Colon cancer stem cells (CSC) were seeded at $3 \times 10^3$;

Testing compounds were added after 24 h and incubated for 72 h (48 h for 697 cell line). The concentrations of molecules ranged from 10000 nM to 1.5 nM (10000 to 1 nM for 697 cell line). The cytotoxic activity of compounds was evaluated using the CellTiter 96® Aqueous One Solution Cell Proliferation Assay (Promega) which measures the functionality of mitochondria according to manufacturer's instructions. For Colon cancer stem cells viability was determined with CellTiter-Glo Luminescent cell viability assay (Promega).

In the primary cytotoxicity screening performed on 697 cell line the activity of compounds D was similar or higher than that of saturated compounds.

The proliferation inhibitory activity of the unsaturated compounds of the present invention on HCT116 cells is 30 to 80 fold higher than the one exhibited by saturated analogues of the prior art U.S. Pat. No. 7,635,788, while it is at least similar or 3.5 to 40 fold higher on the stem cells (see table 1). In particular, all the compounds of the invention are resulted more active than the saturated analogues of the prior art on HCT116 cells.

The compound cytotoxicity was confirmed by further assays on two other colon cancer cell lines HT29 (ATCC HTB38) and Colo205 (ATCC CCL222) and on colon cancer stem cells (CSCs) (see table 2 and 3). It is worth noting that cytotoxic activity toward human primary kidney cells and peripheral blood mononuclear cells (PBMC) isolated from healthy donors was lower compared to tumor cells cytotoxicity (see table 4).

The cis-form prepared according to Example 3 is resulted less potent of the trans-form on HCT116 cells.

Furthermore the cis-form is chemically less stable than the trans. In a force degradation test all the compounds in the trans-form show high stability even at high temperatures (15 days at 80° C.) and at low pH (15 days at pH 2), while cis-analogue was little less stable at 80° C. and definitely less stable at pH 2.

TABLE 1
Comparison results on colon cancer cell lines
| COMPOUND | HCT116 (nM) | CSC1 (nM) | CyTox697 (nM) |
|---|---|---|---|
| 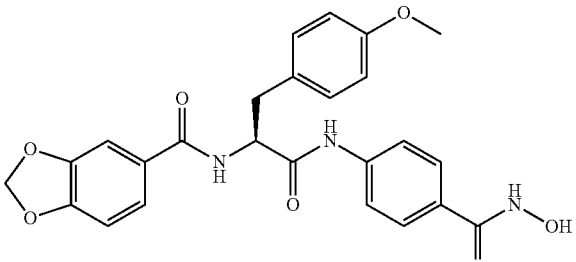 Compound 1A | 24 | 24 | 21 |
| 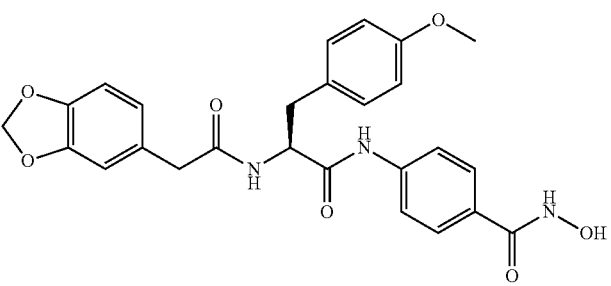 Compound 1B | 554 | 280 | 168 |
| 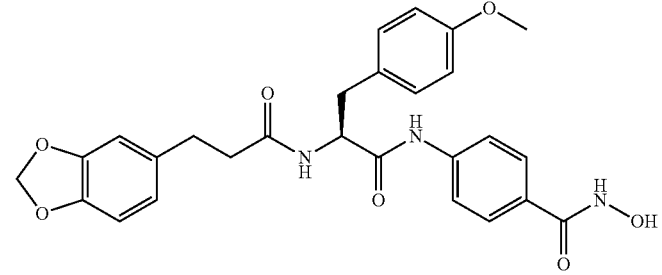 Compound 1C | 702 | 400 | 496 |
| 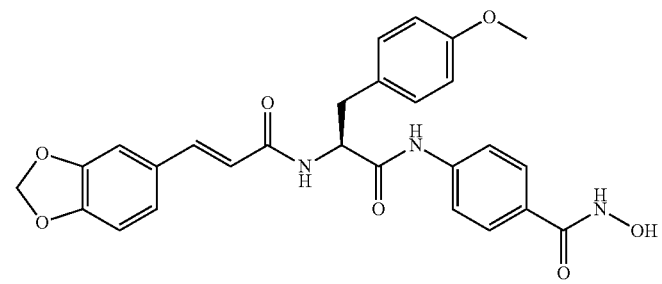 Compound 1D | 18 | 192 | 3 |

TABLE 1-continued
Comparison results on colon cancer cell lines
| COMPOUND | HCT116 (nM) | CSC1 (nM) | CyTox697 (nM) |
|---|---|---|---|
| 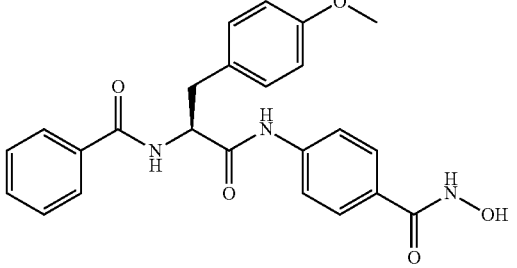 Compound 2A | 76 | 48 | 54 |
| 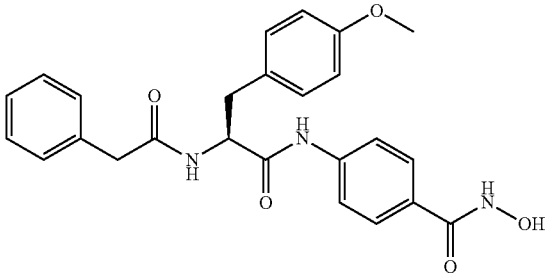 Compound 2B | 316 | 160 | 72 |
| 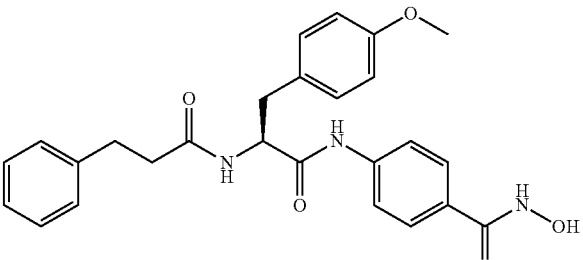 Compound 2C | 431 | 136 | 53 |
| 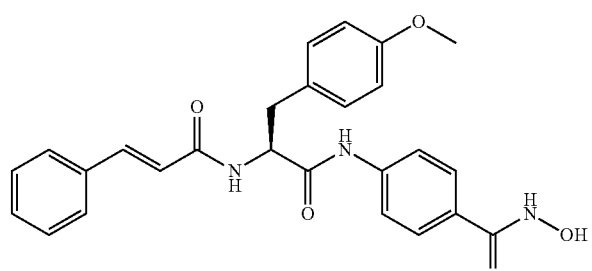 Compound 2D | 13 | 40 | 22 |

TABLE 1-continued

Comparison results on colon cancer cell lines

| COMPOUND | HCT116 (nM) | CSC1 (nM) | CyTox697 (nM) |
|---|---|---|---|
| Compound 3E | 194 | na | 44 |
| Compound 4A | 79 | na | 18 |
| Compound 4B | 1072 | 208 | 127 |
| Compound 4C | 900 | 336 | 203 |

TABLE 1-continued
Comparison results on colon cancer cell lines
| COMPOUND | HCT116 (nM) | CSC1 (nM) | CyTox697 (nM) |
|---|---|---|---|
| 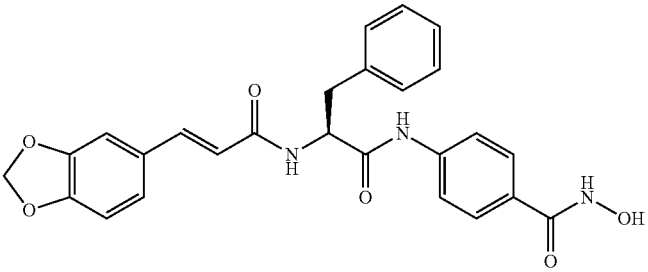 Compound 4D | 11 | 37 | 85 |
| 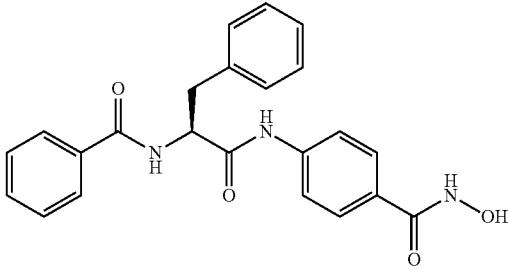 Compound 5A | 184 | 96 | 105 |
| 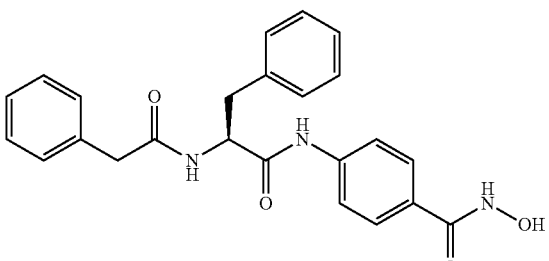 Compound 5B | 237 | 192 | 90 |
| 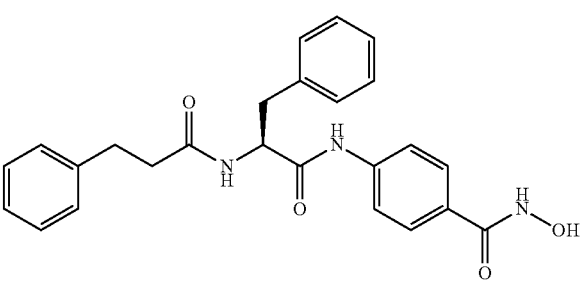 Compound 5C | 806 | 332 | 770 |

TABLE 1-continued

Comparison results on colon cancer cell lines

| COMPOUND | HCT116 (nM) | CSC1 (nM) | CyTox697 (nM) |
|---|---|---|---|
| Compound 5D | 10 | 73 | 45 |
| Compound 6E | 466 | 424 | 59 |

TABLE 2

Cytotoxic activity of compounds on colon cancer cell lines

| Compound | HCT-116 IC 50 (nM) | HT29 IC 50 (nM) | COLO205 IC 50 (nM) |
|---|---|---|---|
| 5D | 14 | 197 | 221 |
| 4D | 19 | 215 | 201 |
| 1D | 18 | 157 | 146 |
| 2D | 14 | 61 | 73 | na=not available

The activity of compounds at any dose is calculated as percentage of inhibition versus vehicle-treated control (=0). The IC50s are extrapolated from the inhibition dose/response curve using GraphPad Prism program.

TABLE 3

Cytotoxic activity of compounds on colon cancer stem cell

| Compound | CSC1 IC 50 (nM) | CSC2 IC 50 (nM) | CSC3 IC 50 (nM) |
|---|---|---|---|
| 5D | 26 | 102 | 230 |
| 4D | 13 | 102 | 91 |
| 1D | 19 | 114 | 85 |
| 2D | 50 | 100 | 70 |

TABLE 4

Cytotoxic activity of compounds on primary renal cells and PBMC

| Compound | PBMC 1 IC 50 (nM) | PBMC 2 IC 50 (nM) | Renal.ep1 IC 50 (nM) | Renal.ep2 IC 50 (nM) |
|---|---|---|---|---|
| 5D | 147 | 595 | 1061 | 511 |
| 4D | 359 | 601 | 778 | na |
| 1D | 80 | 152 | 462 | 321 |
| 2D | 89 | 42 | na | na |

Antitumor Activity In Vivo

The compounds of this invention also showed activity in vivo in a xenograft model of colon cancer where the human HTC116 colorectal carcinoma cell line was injected subcutaneously (sc) in CD1 nude female mice (see table 5).

Female CD-1 nude mice, 5 weeks of age and 20 to 22 g of weight, were housed in the animal house of the Italfarmaco Research Centre. Mice were maintained in micro isolator cages and supplied with sterile food and water under standard conditions.

Xenografts were generated by sc injection of $7 \times 10^6$ HCT116 cells in the right flank of the animals.

Tumor sizes were determined by caliper measurements and tumor volumes were calculated according to the following formula:

$$\text{Tumor volume (mm}^3\text{)} = (w2 \times 1)/2$$

where "w" is the width and "l" is the length of the carcinoma in mm.

Tumor growth was followed by volume measurement three times a week.

Tumor mass reached a measurable size three weeks after transplantation, at this time, treatments began.

Two reference compounds were also used in the experiment. The cinnamic hydroxamic acid panobinostat and 5-FU. The compounds were administered at the MTD according to previous experiments or as described in the literature. As shown in table 5, the compounds of this invention were able to reduce tumor size and volume, their activity being comparable to that of the two reference compounds.

Of note, the treatment with the reference compound 5-FU lead to a remarkable leukopenia (70.4%) at the end of the treatment while compound 4D showed a comparable effectiveness (54% reduction of tumor compared to 61% obtained with 5-FU) but a much less pronounced leukopenia (23.7%).

Furthermore, no thrombocytopenia and no weight loss were observed at the end of the treatment indicating that at the effective doses, the compounds object of this invention exhibited a favourable therapeutic window in this animal model.

The compounds of the present invention show good in vitro metabolic stability, both when incubated with human S9-fraction and in human plasma. They also show a good pharmacokinetic profile in preliminary studies in preclinical species.

The invention claimed is:
1. A compound of the formula (I)

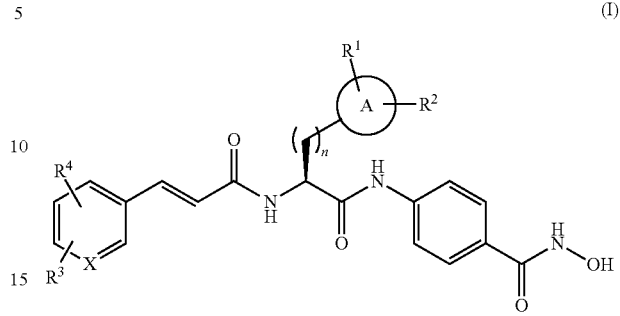

or pharmaceutically acceptable salts, isomers, or prodrugs thereof,
wherein:
n is 0, 1 or 2;
A is a mono or di-carbocyclic residue, optionally partially or totally unsaturated, comprising carbon atoms and optionally one or more heteroatoms selected from N, S or O; or
A is H;
$R^1$ and $R^2$ are independently selected from the group consisting of —H, —OH, —OMe, —CN, —$NH_2$, —$NO_2$, —Cl, —COOH, -halogen, —$CF_3$, —N(Ra)$_2$, linear or branched $C_1$-$C_4$ alkyl, aryl, arylalkyl, arylcarbonyl, alkoxy, aryloxy residue, sulphonylamino and —$CH_2N(CH_2CH_3)_2$;

TABLE 5

| | | | Summary of the anti-tumor in vivo activity | | |
|---|---|---|---|---|---|
| Compound | Dose, route of administration | % inhib tumor vs CTRL after 44 days of treatment | % inhib WBC vs CTRL T$_0$ after 44 days of treatment (vs predose) | % inhib PLT vs CTRL T$_0$ after 44 days of treatment (vs predose) | % of Body Weight variation intragroup After 65 days of treatment |
| Panobinostat | 1 mg/kg, ip | 34 | 36.8 (−7.2) | −4.2 (−20.3) | −1.08 |
| 5D | 5 mg/kg, ip | 46 | 31.8 (−15.7) | −6.4; (−22.9) | 1.73 |
| 4D | 5 mg/kg, ip | 54 | 23.7 (−29.4) | −10.3; (−27.3) | −0.97 |
| 4D | 10 mg/kg, ip | 39 | 25.2 (−26.9) | −6.3, (−22.7) | 1.24 |
| 1D | 0.5 mg/kg, ip | 23 | −11.7 (−89.4) | −14.3; (−31.9) | −0.41 |
| 1D | 1 mg/kg, ip | 22 | 16.2; (−42.1) | −8.3; (−25) | 1.42 |
| 2D | 1 mg/kg, ip | 33 | 1.6; (−67) | 2.8; (−12.2) | −1.84 |
| 5-FU | 10 mg/kg, ip | 36 | 26; (−25.5) | 1.9; (−13.2) | −3.22 |
| 5-FU | 70 mg/kg, ip, once a week | 61 | 70.4; (49.7) | −12.4; (−29.8) | 1.57 |
| CTRL | Vehicle, 200 μL/mice | na | (69.6) | (−15.4) | 6.7 | provided that when A is H, $R^1$ and $R^2$ are absent:

Ra is a linear or branched $C_1$-$C_3$ alkyl residue;

X is C, CH, or N;

$R^3$ and $R^4$ are independently selected from the group consisting of —H, —OMe, —OPh, —NO$_2$, —NMe$_2$, —NH$_2$, -halogen, —CF$_3$, —N(Ra)$_2$, linear or branched $C_1$-$C_4$ alkyl, aryl, arylalkyl, arylcarbonyl, alkoxy, aryloxy residue and sulphonylamino, or $R^3$ and $R^4$ together form a heteropentacyclic moiety comprising —(—OCH$_2$O—).

2. The compound according to claim 1, in which:

$R^1$ and $R^2$ are independently selected from the group consisting of —H, —OH, —OMe, —CN, —NH$_2$, —NO$_2$, —Cl, —COOH and —CH$_2$N(CH$_2$CH$_3$)$_2$;

$R^3$ and $R^4$ are independently selected from the group comprising —H, —OMe, —OPh, —NO$_2$, —NMe$_2$ and —NH$_2$, or $R^3$ and $R^4$ together form a heteropentacyclic moiety comprising —(—OCH$_2$O—).

3. The compound according to claim 1, in which n is 1, X is C or CH;

$R^1$ and $R^2$ are independently —H, —Cl or —OMe; and $R^3$ and $R^4$ are independently —H, —NMe$_2$, or $R^3$ and $R^4$ together form a heteropentacyclic moiety comprising —(—OCH$_2$O—).

4. A compound selected from the group consisting of:

(2S)-2-[[(E)-3-(1,3-benzodioxol-5-yl)prop-2-enoyl]amino]-N-[4-(hydroxycarbamoyl)phenyl]-3-(4-methoxyphenyl)propanamide (1D);

(2S)-N-[4-(hydroxycarbamoyl)phenyl]-3-(4-methoxyphenyl)-2-[[(E)-3-phenylprop-2-enoyl]amino]propanamide (2D);

(2S)-2-[[(E)-3-(1,3-benzodioxol-5-yl)prop-2-enoyl]amino]-N-[4-(hydroxycarbamoyl)phenyl]-3-phenyl-propanamide (4D);

(2S)-N-[4-(hydroxycarbamoyl)phenyl]-3-phenyl-2-[[(E)-3-phenylprop-2-enoyl]amino]propanamide (5D);

(2S)-2-[[(E)-3-(2,5-dimethoxyphenyl)prop-2-enoyl]amino]-N-[4-(hydroxycarbamoyl)phenyl]-3-(4-hydroxyphenyl)propanamide (7D);

(E)-3-(2,5-dimethoxyphenyl)-N-[(1R)-2-[4-(hydroxycarbamoyl)anilino]-1-indan-2-yl-2-oxo-ethyl]prop-2-enamide (8D);

(2S)-2-[[(E)-3-(2,5-dimethoxyphenyl)prop-2-enoyl]amino]-N-[4-(hydroxycarbamoyl)phenyl]-4-phenyl-butanamide (9D);

(2S)-2-[[(E)-3-(2,5-dimethoxyphenyl)prop-2-enoyl]amino]-N-[4-(hydroxycarbamoyl)phenyl]-3-phenyl-propanamide (10D);

(2S)-2-[[(E)-3-(2,5-dimethoxyphenyl)prop-2-enoyl]amino]-N-[4-(hydroxycarbamoyl)phenyl]-3-(2-naphthyl)propanamide (11D);

(E)-3-(2,5-dimethoxyphenyl)-N-[2-[4-(hydroxycarbamoyl)anilino]-2-oxo-ethyl]prop-2-enamide (12D);

(2S)-2-[[(E)-3-(2,5-dimethoxyphenyl)prop-2-enoyl]amino]-N-[4-(hydroxycarbamoyl)phenyl]propanamide (13D);

(2S)-2-[[(E)-3-(2,5-dimethoxyphenyl)prop-2-enoyl]amino]-N-[4-(hydroxycarbamoyl)phenyl]-3-(3-quinolyl)propanamide (14D);

(2S)-2-[[(E)-3-(2,5-dimethoxyphenyl)prop-2-enoyl]amino]-N-[4-(hydroxycarbamoyl)phenyl]-3-(3-pyridyl)propanamide (15D);

(2S)-2-[[(E)-3-(2,5-dimethoxyphenyl)prop-2-enoyl]amino]-N-[4-(hydroxycarbamoyl)phenyl]-3-(4-nitrophenyl)propanamide (16D);

(2S)-2-[[(E)-3-(4-aminophenyl)prop-2-enoyl]amino]-N-[4-(hydroxycarbamoyl)phenyl]-3-phenyl-propanamide (17D);

(2S)-3-(4-aminophenyl)-2-[[(E)-3-(2,5-dimethoxyphenyl)prop-2-enoyl]amino]-N-[4-(hydroxycarbamoyl)phenyl]propanamide (18D);

(2S)-3-(4-cyanophenyl)-2-[[(E)-3-(2,5-dimethoxyphenyl)prop-2-enoyl]amino]-N-[4-(hydroxycarbamoyl)phenyl]propanamide (19D);

(2S)-N-[4-(hydroxycarbamoyl)phenyl]-2-[[(E)-3-(4-nitrophenyl)prop-2-enoyl]amino]-3-phenyl-propanamide (20D);

(2S)-2-[[(E)-3-(2,5-dimethoxyphenyl)prop-2-enoyl]amino]-N-[4-(hydroxycarbamoyl)phenyl]-3-(1H-imidazol-5-yl)propanamide (21D);

(2S)-2-[[(E)-3-(3,4-dimethoxyphenyl)prop-2-enoyl]amino]-N-[4-(hydroxycarbamoyl)phenyl]-3-(3-pyridyl)propanamide (22D);

(2S)-2-[[(E)-3-(3,5-dimethoxyphenyl)prop-2-enoyl]amino]-N-[4-(hydroxycarbamoyl)phenyl]-3-(3-pyridyl)propanamide (23D);

(2S)-2-[[(E)-3-(1,3-benzodioxol-5-yl)prop-2-enoyl]amino]-N-[4-(hydroxycarbamoyl)phenyl]-3-(3-pyridyl)propanamide (24D);

(2S)-2-[[(E)-3-(1,3-benzodioxol-5-yl)prop-2-enoyl]amino]-3-(benzothiophen-3-yl)-N-[4-(hydroxycarbamoyl)phenyl]propanamide (25D);

(2S)-2-[[(E)-3-(1,3-benzodioxol-5-yl)prop-2-enoyl]amino]-N-[4-(hydroxycarbamoyl)phenyl]-3-thiazol-4-yl-propanamide (26D);

(2S)-2-[[(E)-3-(1,3-benzodioxol-5-yl)prop-2-enoyl]amino]-N-[4-(hydroxycarbamoyl)phenyl]-4-phenyl-butanamide (27D);

(2S)-2-[[(E)-3-(3,4-dimethoxyphenyl)prop-2-enoyl]amino]-N-[4-(hydroxycarbamoyl)phenyl]-3-phenyl-propanamide (28D);

(2S)-2-[[(E)-3-(1,3-benzodioxol-5-yl)prop-2-enoyl]amino]-3-(4-cyanophenyl)-N-[4-(hydroxycarbamoyl)phenyl]propanamide (29D);

(2S)-2-[[(E)-3-(3,4-dimethoxyphenyl)prop-2-enoyl]amino]-N-[4-(hydroxycarbamoyl)phenyl]-3-(1H-indol-3-yl)propanamide (30D);

(2S)-2-[[(E)-3-(1,3-benzodioxol-5-yl)prop-2-enoyl]amino]-N-[4-(hydroxycarbamoyl)phenyl]-3-(1H-indol-3-yl)propanamide (31D);

(2S)-2-[[(E)-3-(1,3-benzodioxol-5-yl)prop-2-enoyl]amino]-N-[4-(hydroxycarbamoyl)phenyl]-3-(4-nitrophenyl)propanamide (32D);

(2S)-2-[[(E)-3-(1,3-benzodioxol-5-yl)prop-2-enoyl]amino]-3-(4-chlorophenyl)-N-[4-(hydroxycarbamoyl)phenyl]propanamide (33D);

(2S)-3-(4-aminophenyl)-2-[[(E)-3-(3,4-dimethoxyphenyl)prop-2-enoyl]amino]-N-[4-(hydroxycarbamoyl)phenyl]propanamide (34D);

(2S)-3-(4-aminophenyl)-2-[[(E)-3-(1,3-benzodioxol-5-yl)prop-2-enoyl]amino]-N-[4-(hydroxycarbamoyl)phenyl]propanamide (35D);

4-[(2S)-2-[[(E)-3-(1,3-benzodioxol-5-yl)prop-2-enoyl]amino]-3-[4-(hydroxycarbamoyl)anilino]-3-oxo-propyl]benzoic acid (36D);

(2S)-2-[[(E)-3-(1,3-benzodioxol-5-yl)prop-2-enoyl]amino]-3-(3,4-dichlorophenyl)-N-[4-(hydroxycarbamoyl)phenyl]propanamide (37D);

(2S)-N-[4-(hydroxycarbamoyl)phenyl]-3-(4-methoxyphenyl)-2-[[(E)-3-phenylprop-2-enoyl]amino]propanamide (38D);

(2S)-2-[[(E)-3-(4-dimethylaminophenyl)prop-2-enoyl]amino]-N-[4-(hydroxycarbamoyl)phenyl]-3-phenyl-propanamide (39D);

(2S)-2-[[(E)-3-(4-dimethylaminophenyl)prop-2-enoyl]amino]-N-[4-(hydroxycarbamoyl)phenyl]-3-(4-methoxyphenyl)propanamide; 2,2,2-trifluoroacetic acid (40D);

(E)-N-[2-[[4-(hydroxycarbamoyl)phenyl]methylamino]-2-oxo-ethyl]-3-phenyl-prop-2-enamide (41D);

(E)-3-(1,3-benzodioxol-5-yl)-N-[2-[[4-(hydroxycarbamoyl)phenyl]methylamino]-2-oxo-ethyl]prop-2-enamide (43D);

(2 S)-3-[4-(diethylaminomethyl)phenyl]-N-[4-(hydroxycarbamoyl)phenyl]-2-[[(E)-3-phenylprop-2-enoyl]amino]propanamide; 2,2,2-trifluoroacetic acid (45D);

(2S)-2-[[(E)-3-(1,3-benzodioxol-5-yl)prop-2-enoyl]amino]-3-[4-(diethylaminomethyl)phenyl]-N-[4-(hydroxycarbamoyl)phenyl]propanamide; 2,2,2-trifluoroacetic acid (46D);

(2S)-N-[4-(hydroxycarbamoyl)phenyl]-3-(2-naphthyl)-2-[[(E)-3-(6-phenoxy-3-pyridyl)prop-2-enoyl]amino]propanamide (47D).

5. The compound according to claim 1, in which the isomeric form is a trans-form.

6. A pharmaceutical composition comprising a therapeutically effective quantity of at least one of the compounds of the formula (I) or pharmaceutically acceptable salts, isomers or prodrugs thereof according to claim 1 together with at least one pharmaceutically acceptable excipient.

7. The pharmaceutical composition according to claim 6, in a form of an enteral formulation, parenteral formulation, oral formulation, topical formulation, or inhalatory formulation.

8. The pharmaceutical composition according to claim 6, in a form of a liquid or a solid.

9. The pharmaceutical composition according to claim 6, in a form of capsules, tablets, coated tablets, powders, granules, creams or ointments.

10. A method for treating colorectal cancer or hematologic malignancies, comprising the step of administering a therapeutically effective amount of the compound of claim 1 to a patient in need thereof.

* * * * *